(12) United States Patent
Peretto

(10) Patent No.: US 8,585,603 B2
(45) Date of Patent: *Nov. 19, 2013

(54) NONINVASIVE APPARATUS AND METHOD FOR ESTIMATING BLOOD PRESSURE

(75) Inventor: Lorenzo Peretto, Fratta Polesine (IT)

(73) Assignee: Luca Longhini, Ferrara (IT)

( * ) Notice: Subject to any disclaimer, the term of this patent is extended or adjusted under 35 U.S.C. 154(b) by 1864 days.

This patent is subject to a terminal disclaimer.

(21) Appl. No.: 11/881,848

(22) Filed: Jul. 30, 2007

(65) Prior Publication Data

US 2008/0027333 A1    Jan. 31, 2008

Related U.S. Application Data

(63) Continuation-in-part of application No. 11/496,754, filed on Aug. 1, 2006, now Pat. No. 7,828,740.

(60) Provisional application No. 60/704,921, filed on Aug. 3, 2005.

(51) Int. Cl.
*A61B 5/02* (2006.01)

(52) U.S. Cl.
USPC .......................................... 600/485; 600/528

(58) Field of Classification Search
USPC ......... 600/485, 493–496, 508, 513–514, 528, 600/586; 607/18–24; 704/211–218; 700/94
See application file for complete search history.

(56) References Cited

U.S. PATENT DOCUMENTS

| | | | |
|---|---|---|---|
| 5,109,863 A * | 5/1992 | Semmlow et al. ............ | 600/528 |
| 6,050,950 A | 4/2000 | Mohler | |
| 6,368,283 B1 * | 4/2002 | Xu et al. ....................... | 600/485 |
| 2004/0127792 A1 * | 7/2004 | Siejko et al. .................. | 600/439 |
| 2004/0167417 A1 | 8/2004 | Schulhauser et al. | |
| 2004/0267148 A1 * | 12/2004 | Arand et al. .................. | 600/528 |
| 2005/0148896 A1 * | 7/2005 | Siejko et al. .................. | 600/528 |
| 2005/0222515 A1 * | 10/2005 | Polyshchuk et al. .......... | 600/528 |

FOREIGN PATENT DOCUMENTS

WO    WO 2007/015153 A2    2/2007

OTHER PUBLICATIONS

Longhini et al. "A New Noninvasive Method for Estimation of Pulmonary Arterial Pressure in Mitral Stenosis" Aug. 1991. Amer. J. Cardiology. vol. 68, Issue 4, pp. 398-401.*
European Patent Office Communication relating to EPO Application No. 07 866 573.4 dated Jul. 30, 2010.
A New Noninvasive Method for Estimation of Pulmonary Arterial Pressure in Mitral Stenosis; by: Carlo Longhini, et al.; The American Journal of Cardiology vol. 68, (Aug. 1, 1991) pp. 398-401.
A new, simple, and accurate method for non-invasive estimation of pulmonary arterial pressure; J. Xu et al.; www.hearinl.com, (Heart 2002) vol. 88; pp. 76-80.

(Continued)

*Primary Examiner* — Navin Natnithithadha
*Assistant Examiner* — Eric Messersmith
(74) *Attorney, Agent, or Firm* — RatnerPrestia

(57) ABSTRACT

Methods and apparatus for noninvasively estimating a blood pressure are provided. A target interval is determined from a diastolic signal such that the target interval includes an S2 component. The S2 component is extracted from the diastolic signal using the target interval and is analyzed in the target interval to obtain a number of oscillations in the S2 component. A predetermined relationship between the number of oscillations in the S2 component and blood pressure is used to generate a blood pressure estimate.

30 Claims, 13 Drawing Sheets

(56) References Cited

OTHER PUBLICATIONS

Noninvasive Estimation of the Pulmonary Systolic Pressure From the Spectral Analysis of the Second Hear Sound; S. Aggio et al.; Acta Cardiologica, vol. XLV, 1990, 3 pp. 199-202.

Estimation of Pulmonary Artery Pressure by Spectral Analysis of the Second Heart Sound; Danmin Chen, et al.; The American Journal of Cardiology, vol. 78, (Oct. 1, 1996) pp. 785-789.

"Automated Extraction of Aortic and Pulmonary Components of the Second Heart Sound for the Estimation of Pulmonary Artery Pressure" B. Popov et al. Conference Proceedings. 26th Annual International Conference of the IEEE Engineering in Medicine and Biology Society (IEEE Cat. No. 04CH37558) IEEE Piscataway, NJ, USA. vol. 2, 2004, p. 921-924. ISBN: 07803-8439-3.

International Search Report corresponding to PCT/IB2006/002111 dated Jan. 24, 2007.

International Search Report Corresponding to PCT/IB2007/004048 dated Jul. 10, 2008.

* cited by examiner

NONINVASIVE APPARATUS AND METHOD FOR ESTIMATING BLOOD PRESSURE

CROSS REFERENCE TO RELATED APPLICATIONS

This application is a continuation in part of U.S. Nonprovisional application Ser. No. 11/496,754 filed on Aug. 1, 2006 now U.S. Pat. No. 7,828,740 and which is related to and claims the benefit of U.S. Provisional Application No. 60/704,921 entitled NONINVASIVE APPARATUS FOR THE PULMONARY ARTERY PRESSURE MEASUREMENT filed on Aug. 3, 2005, the contents of which are incorporated herein by reference.

FIELD OF THE INVENTION

The present invention relates to the field of clinical evaluation of cardiac diseases and, more particularly, to methods and apparatus for noninvasively estimating the pulmonary artery pressure.

BACKGROUND OF THE INVENTION

Pulmonary artery pressure (PAP) measurements are known in the art and have been used for a number of years to aid in the diagnosis of cardiac and pulmonary diseases. A PAP measurement may be obtained through an invasive procedure, such as using a pulmonary arterial catheter (e.g. Swan-Ganz catheter). A PAP estimation may also be obtained through a noninvasive procedure, for example, using Doppler Echocardiography, in order to estimate the PAP via known-in-the-art ultrasound techniques. In addition, methods using heart sounds analysis have also been proposed. For example, see U.S. Pat. No. 6,368,283 to Xu et al., entitled "Method and apparatus for estimating systolic and mean pulmonary artery pressures of a patient."

Invasive procedures, however, are typically uncomfortable for the patient. Pulmonary artery catheterization, for example, even in skilled hands, may carry various risks and complications.

Doppler Echocardiography, may not be efficacious in the absence of a Doppler-detectable tricuspid valve regurgitation. Furthermore, the values of systolic PAP are only approximate because a clinical estimation of the right atrial (RA) pressure is typically necessary. This may be a potential source of error in the estimation of the real PAP in a patient. Furthermore, a good acoustic window and satisfactory flow tracing are typical factors used to adequately locate the tricuspid regurgitant jet. These factors, however, may be suboptimal in persons with pulmonary hyperinflation, or in those persons who are obese, because of poor transmission of sound waves.

Both conventional invasive and noninvasive procedures typically require highly skilled personnel (i.e. physicians or technicians) as well as the utilization of expensive equipment. Cardiac catheterization may also require use of a suitably equipped operating room, with attending operating room personnel.

SUMMARY OF THE INVENTION

The present invention is embodied in a method and apparatus for noninvasively estimating a blood pressure. The method includes the steps of a) extracting a pulmonic (P) subcomponent from a diastolic signal and b) analyzing the extracted P subcomponent to obtain a number of oscillations in the P subcomponent. The method further includes the step of c) applying a predetermined relationship between the obtained number of oscillations and blood pressure to generate a blood pressure estimate.

The present invention is further embodied in an apparatus for receiving heart sounds from a chest wall. The apparatus includes a sensor coupled to the chest wall and configured to receive heart sounds from the chest wall and a cover disposed over the sensor and coupled to the chest wall. The apparatus further includes adjusting means for adjusting the pressure of the sensor on the chest wall within the cover and holding means for coupling the cover to the chest wall. The holding means and the cover tend to increase a transmission of the heart sounds from the chest wall to the sensor relative to the sensor without the holding means or the cover.

The present invention is also embodied in further methods and apparatus for noninvasively estimating a blood pressure. The method includes the steps of determining a target interval from a diastolic signal such that the target interval includes a second heart sound (S2) component, extracting the S2 component from the diastolic signal using the target interval and analyzing the extracted S2 component in the target interval to obtain a number of oscillations in the extracted S2 component. The method applies a predetermined relationship between the obtained number of oscillations and blood pressure to generate and display a blood pressure estimate.

BRIEF DESCRIPTION OF THE DRAWINGS

The invention is best understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover in the drawings, common numerical references are used to represent like features/elements. Included in the drawing are the following figures.

DETAILED DESCRIPTION OF THE INVENTION

Figure 1A:
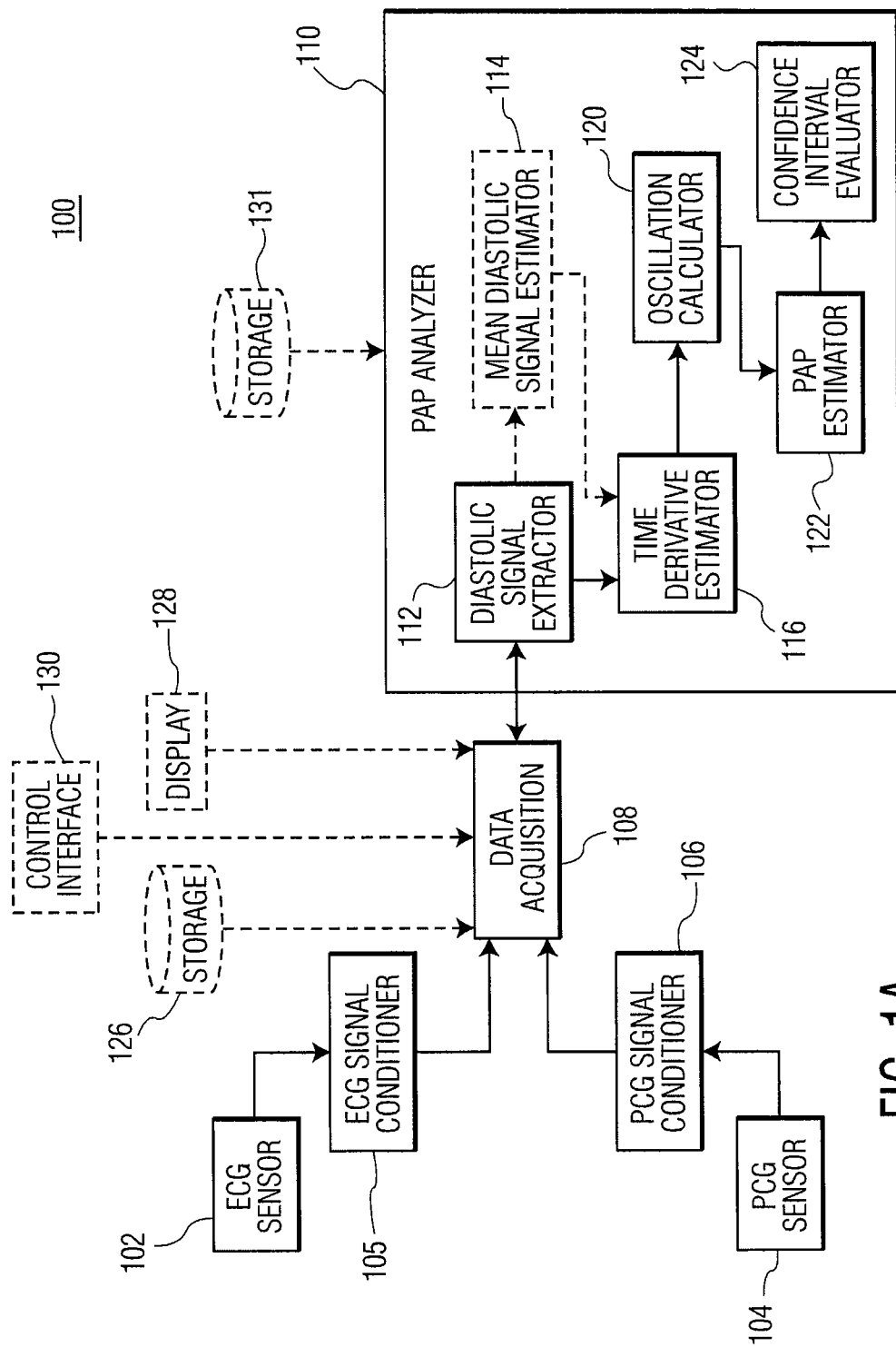
FIGS. 1A, 1B and 1C are functional block diagrams illustrating an exemplary apparatus for noninvasively estimating a pulmonary artery pressure (PAP) according to an embodiment of the present invention.

The present invention is embodied in methods and apparatus for noninvasively estimating blood pressure and, desirably, PAP. First, an exemplary system and methods for estimating PAP is described. Second, an exemplary PCG sensor is described. Third, exemplary ECG and PCG signal conditioners are described. Fourth, an exemplary connection module of a data acquisition system is described. Fifth, a method for performing data acquisition using a short-range connection is described. Sixth, a further exemplary system and methods for noninvasively estimating PAP are described.

The second heart sound (S2) component, generated by both the aortic and myocardium valves and by the pulmonary valve, is typically transmitted to the surrounding body, including the chest wall, through the right side of the heart, i.e., the pulmonary atrium and ventricle. Because the thickness of the left side of the heart is much greater than the thickness of the right side of the heart, the S2 component, through the left side, may be attenuated and low-pass filtered in transmission to the chest wall. Accordingly, sounds originating inside the heart may generally be transmitted to the chest wall through the right atrium and ventricle walls.

Typically, the S2 component includes an aortic (A) subcomponent, corresponding to closure of the aortic valve, and a pulmonary (P) subcomponent, corresponding to closure of the pulmonary valve. Generally, in an S2 component that is transmitted to the chest wall, the A subcomponent precedes the P subcomponent. In some instances, the P subcomponent may precede the A subcomponent or the A and P subcomponents may appear to occur simultaneously.

For the S2 component, both the aortic and pulmonary valves feature similar characteristics and biological composition. The aortic and pulmonary valves typically generate sounds with similar spectral composition. However, aortic valve sounds are mainly transmitted outside the heart through its right side walls, passing through the ventricles separation walls, which, in turn, modifies the spectral content as compared with sounds generated by the pulmonary valve. This leads to an S2 component which includes aortic (A) and pulmonary (P) subcomponents with very similar spectral content. Accordingly, the spectral content of heart sounds, generally, are a function of the elements surrounding the heart itself, such as muscle, organ walls and tissue. The inventors have determined that a number of oscillations of at least the P subcomponent may be used to correlate a frequency composition of the S2 component with the PAP. The estimated PAP may thus include both low and high vibration modes of the sounds of the aortic and pulmonary valves (described further below).

According to the present invention, PAP may be estimated by simultaneously measuring electrocardiogram (ECG) and phonocardiogram (PCG) signals from respective ECG and PCG sensors. A diastolic signal may be extracted from the PCG signal using the QRS complex of the ECG signal. In general, the diastolic signal includes the S2 component and may include a portion of the diastolic interval. The diastolic signal may also include a portion of the systolic interval, i.e. prior to the S2 component. According to one embodiment, a number of oscillations of the pulmonary (P) subcomponent, extracted from the diastolic signal, is desirably determined using the time-domain diastolic signal. A PAP estimate may be generated using a predetermined relationship between the number of oscillations and the PAP. In an exemplary embodiment, the PCG sensor desirably includes a mechanical filter, adjusting means and holding means to reduce background noise and increase the transmission of heart sounds to the PCG sensor. In a further exemplary embodiment, a number of PCG and corresponding ECG signals are acquired and analyzed in order to generate the PAP estimate. According to another embodiment, a number of oscillations of an S2 component (including the A subcomponent and the P subcomponent), isolated from the diastolic signal, is desirably determined. The PAP estimate may be generated using a predetermined relationship between the number of oscillations of the S2 component and the PAP.

Although the present invention describes methods and apparatus for PAP estimation, it is contemplated that the present invention may be used for any blood pressure measurement such as systemic pressure, PAP being only one example of such a blood pressure measurement. It is contemplated that a predetermined relationship may be determined between the number of oscillations and blood pressure to determine a blood pressure estimate.

Figure 1B:
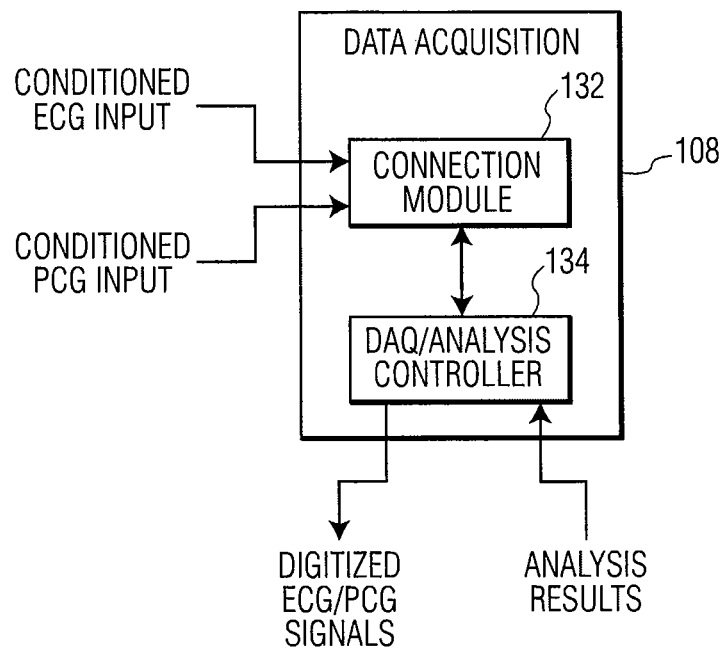
Figure 1C:
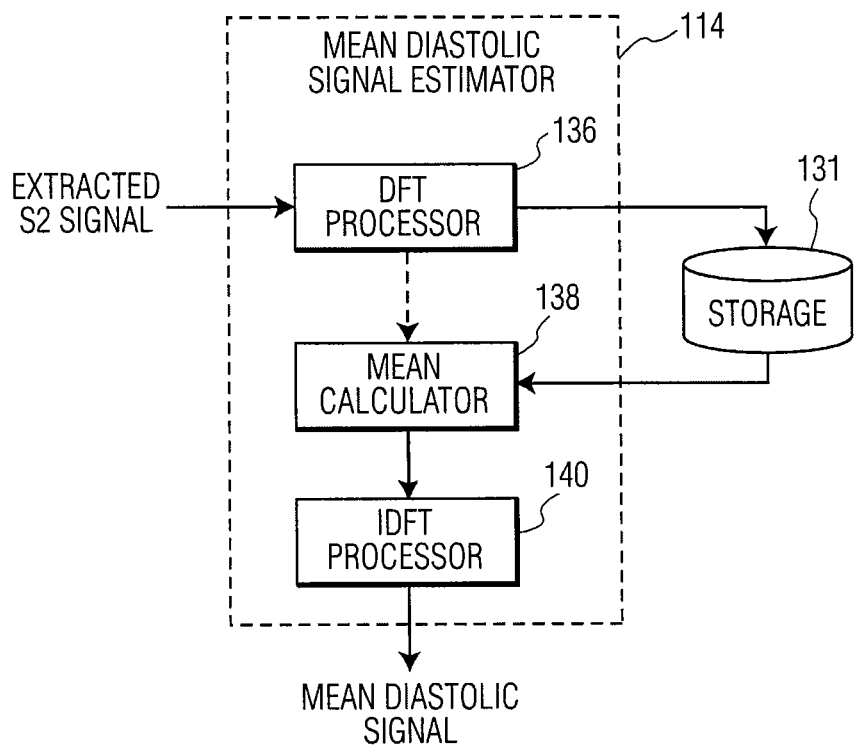

FIGS. 1A, 1B and 1C are functional block diagrams illustrating an exemplary apparatus 100 for noninvasively estimating a PAP according to an embodiment of the present invention. More particularly, FIG. 1A is a functional block diagram of exemplary apparatus 100; FIG. 1B is a functional block diagram of data acquisition system 108; and FIG. 1C is a functional block diagram of mean diastolic signal estimator 114.

Referring to FIG. 1A, an ECG signal from ECG sensor 102 is provided to ECG signal conditioner 105 (described further below) and subsequently the conditioned ECG signal is provided to a data acquisition system 108. A PCG signal from PCG sensor 104 is provided to PCG signal conditioner 106 (described further below) and subsequently the conditioned PCG signal is provided to data acquisition system 108. The PCG signal is desirably synchronously acquired with the ECG signal by data acquisition system 108.

The ECG signal is typically a multilead ECG signal. In an exemplary embodiment ECG sensor 102 consists of three electrodes having three-leads transmitted to the ECG signal conditioner 105. It is understood that the ECG sensor 102 may include any desired number of electrodes for obtaining appropriate ECG signals for determining a QRS complex. It is understood that the ECG electrodes are provided at suitable locations on the chest wall for obtaining the multilead ECG signal. The PCG sensor 104 is described further below with respect to FIG. 2A.

Data acquisition system 108 acquires and digitizes the conditioned ECG and PCG signals and provides the signals to PAP analyzer 110. The PAP analyzer 110 desirably generates a PAP estimate using the digitized PCG and corresponding digitized ECG signals received from the data acquisition system 108.

In an exemplary embodiment, the data acquisition system 108 and PAP analyzer 110 are configured to connect to a network, including a global information network, e.g. the Internet (not shown) for respectively transmitting and receiving the digitized ECG and PCG signals, as well as transmitting a PAP estimate, an extracted diastolic signal, a P subcomponent and a confidence interval (described further below) to the data acquisition system 108 by the PAP analyzer 110. It is contemplated, however, that the data acquisition system 108 may be connected to the PAP analyzer 110 via any wired or wireless connection.

Although FIG. 1A illustrates a single input port to PAP analyzer 110 for receiving the digitized ECG and digitized PCG signals, it is contemplated that PAP analyzer 110 may include multiple input ports each capable of receiving one or more of the digitized ECG and digitized PCG signals. It is further contemplated that PAP analyzer 110 may further perform some or all of the acquisition and digitization functions of the data acquisition system 108.

The data acquisition system 108 may optionally include storage means 126 for storing, for example, the PAP estimate, an extracted diastolic signal (described further below), a P subcomponent, the digitized PCG signal and/or the digitized ECG signal. It is contemplated that storage means 126 may be a memory, a magnetic disk, a database or a further storage means on a remote device, such as a device corresponding to the display 128.

The data acquisition system 108 may optionally include a display 128 for presenting, for example, the PAP estimate, an extracted diastolic signal (described further below), a P subcomponent, the digitized PCG signal and/or the digitized ECG signal. The display 128 may further present control parameters for controlling the data acquisition. Control parameters may include, for example, an acquisition period duration, a number of PCG and ECG signals to be acquired and an exemplary method (described further below) for obtaining a PAP estimate from a plurality of acquired PCG and ECG signals. The display 128 may include one or more light emitting diodes (LEDs) for providing visual confirmation or error notification during the data acquisition process. It is contemplated that display 128 may include any display capable of presenting information including textual and/or graphical information. Although not shown, the data acquisition system 108 may also include an audio output for providing heart sounds and/or audible confirmation or error notification during the data acquisition process.

The data acquisition system 108 may optionally include a control interface 130 for providing control parameters to the data acquisition system 108 and/or for providing further control parameters to the PAP analyzer 110 (not shown), for example, selecting a method for obtaining a PAP estimate. Control interface 130 may further select signals to be displayed and/or stored. The control interface may include a pointing device type interface for selecting control parameters, display parameters and/or storage parameters using display 128. Control interface 130 may further include a text interface for entering information regarding the acquired signals as well as patient information and a filename for storing acquired and/or analyzed data in storage means 126.

It is contemplated that the data acquisition system 108 and/or PAP analyzer 110 may be configured to connect to the Internet (not shown) such that the generated PAP estimate, an extracted diastolic signal (described further below), a P subcomponent, the digitized PCG signal and/or the digitized ECG signal may also be transmitted to a remote location for further processing and/or storage.

In an exemplary embodiment, the PAP analyzer 110 is connected to a global information network (e.g. the Internet) such that the acquired and/or analyzed data may be transmitted to data acquisition system 108. Although in an exemplary embodiment the PAP analyzer 110 includes an Internet connection, it is contemplated that transmission of acquired and analyzed data via an output port of PAP analyzer 110 may be provided by any wireless or wired connection.

In an exemplary embodiment, the PAP analyzer 110 includes a computer that may execute, for example, Java™ software or MATLAB™ software to generate the PAP estimate and the data acquisition system 108 includes a personal digital assistant (PDA) type computer where the storage means 126, display 128 and control interface 130 may be part of the PDA type computer. It is contemplated that PAP analyzer 110 may include any computer including a processor for generating a PAP estimate from the digitized ECG and digitized PCG signals using an algorithm in accordance with the subject invention. The PAP analyzer 110 may include electronic components and any software suitable for performing at least part of the functions of generating a PAP estimate.

Referring now to FIG. 1B, the data acquisition system 108 includes a connection module 132 for receiving analog conditioned PCG and ECG signals and digitizing the signals, for example with an analog to digital converter (ADC) (not shown). The connection module 132 of the exemplary embodiment configures the data acquisition system 108 to receive a differential ECG signal (described further below) and a PCG signal. It is contemplated that any suitable connection module 132 capable of acquiring and digitizing a differential ECG signal and a PCG signal may be used.

Data acquisition system 108 further includes a data acquisition (DAQ)/analysis controller 134 for controlling data acquisition of the ECG and PCG signals and analysis control for transmitting the digitized PCG and ECG signals to the PAP analyzer 110 and receiving the PAP results from the PAP analyzer 110. The DAQ/analysis controller 134 may also control storage of the results in storage means 126 and presentation of results on display 128. The DAQ/analysis controller 134 may also be coupled to control interface 130 for receiving data acquisition and/or analysis parameters. In an exemplary embodiment, DAQ/analysis controller 134 includes a personal digital assistant (PDA) type computer where the storage means 126, display 128 and control interface 130 may be part of the PDA type computer. In an exemplary embodiment, the received ECG signal is also normalized in the DAQ/analysis controller 134. In an exemplary the DAQ/analysis controller 134 includes software, provided in a LabVIEW™ environment, for performing one or more of the functions of the DAQ/analysis controller. It is contemplated that any suitable controller, such as a personal computer, may be used that is capable of controlling data acquisition, transmitting the acquired data, controlling analysis parameters for PAP analyzer 110 and receiving the analysis results.

In an exemplary embodiment, the data acquisition system 108 acquires the PCG and ECG signals at a 44.1 kHz sampling rate and for an acquisition period of 2 s. It is contemplated that the sampling rate may be any suitable sampling rate to capture the frequencies of the diastolic signal and that the acquisition period may include any acquisition period suitable to acquire at least one diastolic signal.

Referring back to FIG. 1A, the PAP analyzer 110 receives digitized PCG and digitized ECG signals from data acquisition system 108. The PAP analyzer includes a diastolic signal extractor 112 that is configured to extract a diastolic signal from the received digitized PCG signal using the received digitized ECG signal. In one exemplary embodiment, two consecutive QRS complexes are identified in the digitized ECG signal and used to provide a timing window for extracting the diastolic signal from the digitized PCG signal (described further below). The extracted diastolic signal is provided to time derivative estimator 116.

In one embodiment, time derivative estimator 116 receives the extracted diastolic signal from diastolic signal extractor 112 and estimates a time derivative of the extracted diastolic signal (described further below). According to one embodiment, time derivative estimator includes a P subcomponent extractor (not shown) that extracts the P subcomponent from the time derivative of the diastolic signal. As described in copending U.S. application Ser. No. 11/496,754, the P subcomponent extractor may use the time derivative to determine the onset time of the P subcomponent within the diastolic signal and to select a predetermined portion of the diastolic signal as the P subcomponent. The extracted P subcomponent is provided to oscillation calculator 120.

In one embodiment, the oscillation calculator 120 desirably determines a number of oscillations in the extracted P subcomponent received from time derivative estimator 116 according to a time domain analysis of the P subcomponent within the diastolic signal. In an exemplary embodiment, the P subcomponent extracted in time derivative estimator 116 provides a time derivative of the P subcomponent of the diastolic signal to oscillation calculator 120. According to one embodiment, the oscillation calculator 120 determines the number of oscillations using the time derivative of the P subcomponent. The number of oscillations determined by the oscillation calculator 120 is provided to PAP estimator 122.

According to one embodiment, the PAP estimator 122 desirably generates a PAP estimate by applying a predetermined relationship between PAP and the number of oscillations from the P subcomponent received from oscillation calculator 120. The predetermined relationship is described in copending U.S. application Ser. No. 11/496,754. It is contemplated that the predetermined relationship may be stored in storage means 131 and retrieved by PAP estimator 122 during generation of the PAP estimate. The PAP estimate may be provided to storage means 126 and/or display 128.

In an exemplary embodiment, a predetermined number of PCG signals and corresponding ECG signals are acquired from ECG sensor 102 and PCG sensor 104 using data acquisition system 108 and processed by PAP analyzer 110 in order to reduce noise artifacts that may be encountered during a single PCG signal and corresponding ECG signal acquisition. For example, noise artifacts may include respiration, patient movement, sensor movement as well as other physiological sounds and background noise that may be added to the PCG and/or ECG signals during one acquisition period. Accordingly, a predetermined number of PCG and ECG signals may be acquired. In an exemplary embodiment, the predetermined number of PCG and ECG signals includes a range of about 50-70. It is contemplated that fewer or more signals may be acquired and processed depending upon the recording conditions as well as background noise.

In an exemplary embodiment, the PAP analyzer 110 may process the predetermined number of PCG signals and corresponding ECG signals to generate a plurality of PAP estimates. The plurality of PAP estimates may be stored in storage means 131. PAP analyzer 110 may include a confidence interval evaluator 124 to evaluate a confidence interval measure from the plurality of PAP estimates generated using the predetermined number of acquired signals. For example, the confidence interval measure may provide high and low PAP estimates within a confidence interval from the PAP estimates. The confidence interval measure may be provided by interval evaluator 124 to storage means 126 and/or display 128. Although illustrated with respect to a plurality of PAP estimates, it is contemplated that a confidence interval measure may be provided for a single PAP estimate.

In an alternative embodiment, PAP analyzer 110 may include a mean diastolic signal estimator 114 that may be configured to determine a mean diastolic signal by calculating the arithmetic mean of a plurality of extracted diastolic signals received from diastolic signal extractor 112, where the plurality of extracted diastolic signals corresponds to the predetermined number of acquired signals. Referring to FIG. 1C, each of the extracted diastolic signals may be provided to a discrete Fourier transform (DFT) processor 136 to generate a DFT signal of the extracted diastolic signal. The DFT signals may be stored in storage means 131. When a predetermined number of diastolic signals are extracted, the plurality of DFT signals may be provided to mean calculator 138 in order to calculate a mean DFT signal from the stored plurality of DFT signals. The mean DFT signal is provided to inverse DFT (IDFT) processor 140. IDFT processor 140 desirably generates an IDFT from the mean DFT signal in order to form a time-domain mean diastolic signal.

It is contemplated that mean calculator 138 may include an accumulator (not shown) and that each DFT signal may be directly provided to the accumulator rather than to storage means 131 in order to generate a summation of the DFT signals as they are generated. The mean calculator 138 may further include a multiplier for generating a mean DFT signal from the summed DFT signals provided by the accumulator.

Referring back to FIG. 1A, the mean diastolic signal may be provided to time derivative estimator 116 and processing through PAP analyzer 110 blocks 116-122 may continue as described above using the mean diastolic signal determined by mean diastolic signal estimator 114.

Figure 2A:
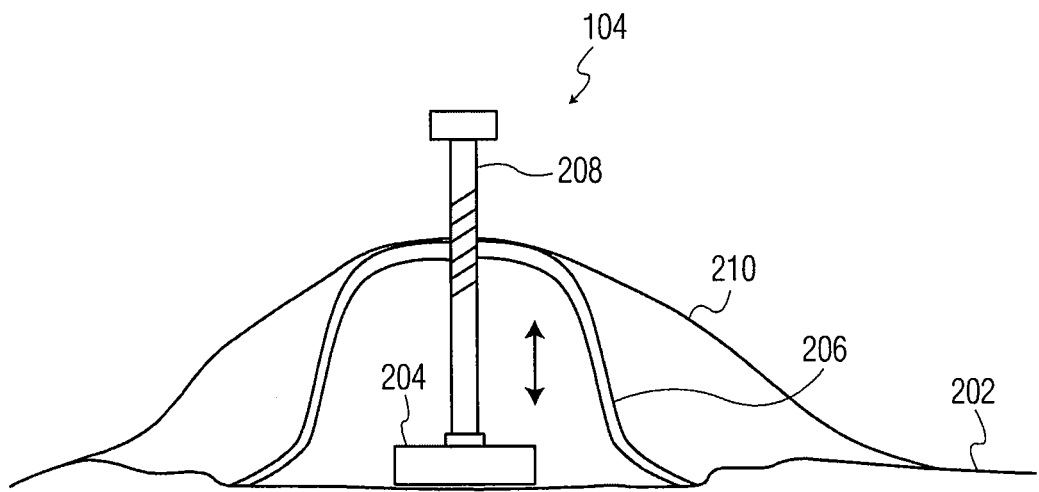
FIG. 2A is a cut-away side plan drawing illustrating an exemplary phonocardiogram (PCG) sensor shown in FIG. 1A, according to an embodiment of the present invention.

FIG. 2A is a cut-away side plan drawing illustrating an exemplary PCG sensor 104 (FIG. 1A) for receiving heart sounds, according to an embodiment of the present invention. A sensor 204 is desirably coupled to receive heart sounds through chest wall 202. The sensor 204 is desirably provided within a cover 206 that may act as a mechanical filter. In an exemplary embodiment, sensor 204 is a piezoelectric transducer available from BIOPAC Systems, Inc., model number SS17L. It is contemplated that sensor 204 may be any sensor capable of receiving heart sounds and transducing the heart sounds into an electrical signal where the sensor has a sensitivity and frequency range suitable for transducing heart sounds.

In an exemplary embodiment, the cover 206 is a bell-shaped cover 206 disposed over the sensor. A lip of the cover 206 is desirable coupled to the chest wall in order to increase a transmission of heart sounds from the chest wall 202 to the sensor 204. The cover 206 also desirably attenuates background noise transmitted to the sensor 204. By coupling cover 206 to the chest wall 202, the cover 206 may mitigate a low-pass filter effect on the transmitted heart sounds by the underlying tissue (i.e. below chest wall 202). Although cover 206 is illustrated as being bell-shaped, it is contemplated that the cover 206 may be any suitably shaped cover capable of reducing background noise and increasing a transmission of the heart sounds to the sensor 204.

The pressure of the sensor 204 on the chest wall 202 is desirably adjusted using adjusting means 208. By adjusting the pressure, a coupling, and thus the fidelity of heart sound transmission to the sensor 204 may be increased. In an exemplary embodiment, adjusting means 208 includes a screw that engages female threads (not shown) in an opening of cover 206, allowing the pressure of the sensor 204 on the chest wall 202 to be adjusted. It is contemplated that the adjusting means 208 may include a spring having a suitable spring constant for automatically adjusting the pressure of the sensor 204 on chest wall 202 to maintain a suitable coupling. It is understood that any adjusting means capable of providing suitable coupling of the sensor 204 to the chest wall 202 to ensure accurate transmission of heart sounds from the chest wall 202 to the sensor 204 may be used.

Although FIG. 2A shows adjusting means 208 extending through the cover 206, it is contemplated that the adjusting means may be placed within cover 206 if adjustment of the sensor coupling is not used, for example, if a spring is used to apply the coupling force. A gel (not shown) may be provided between the sensor 204 and chest wall 202 in order to increase heart sound transmission to the sensor 204. A cable (not shown) may be provided to connect sensor 204 to signal conditioner 106.

PCG sensor 104 may further include a holding means 210 for coupling the cover 206 to the chest wall 202. In an exemplary embodiment, the holding means 210 includes an adhesive belt for securing the cover, and, thus the sensor 204, to the chest wall 202 by wrapping the belt around the patient and over the cover 206. It is contemplated that the holding means 210 may include any means to secure the cover 206 to chest wall 202 while permitting adjustment of the sensor 204 using adjusting means 208. For example, holding means 210 may include an adhesive tape attached between the chest wall 202 and the cover 206. It is further contemplated that the lip of cover 206 that is coupled to the chest wall 202 may include an adhesive material to form the holding means 206. It is also contemplated that the holding means 210 may include a vacuum system to secure the cover 206 to chest wall 202. A vacuum system may further inhibit the transmission of background noise to the sensor 204.

Figure 2B:
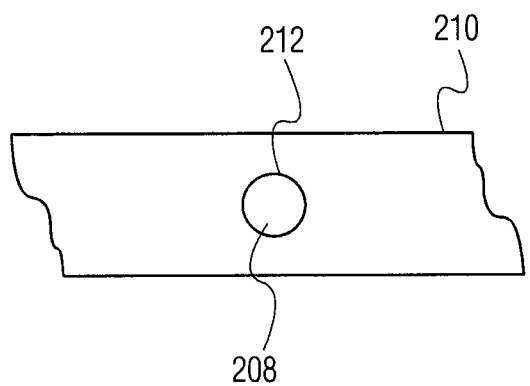
FIG. 2B is an overhead plan drawing illustrating an exemplary holding means shown in FIG. 2A, according to an embodiment of the present invention.

FIG. 2B is an overhead plan drawing illustrating an exemplary holding means 210 shown in FIG. 2A, according to an embodiment of the present invention. Holding means 210 may include an aperture 212 for receiving adjusting means 208 so that holding means 210 may be directly coupled to the cover 206. In this manner, the cover 206 may be secured to the chest wall 202 free of movement along the chest wall 202.

The exemplary PCG sensor 104 shown in FIG. 2A desirably increases the transmission of heart sounds to sensor 204 through the use of the adjusting means 208 and holding means 210, for example, by reducing any attenuation and/or distortion effects provided by the underlying tissue. In addition, the cover 206 may attenuate background noise to sensor 204.

Figure 3A:
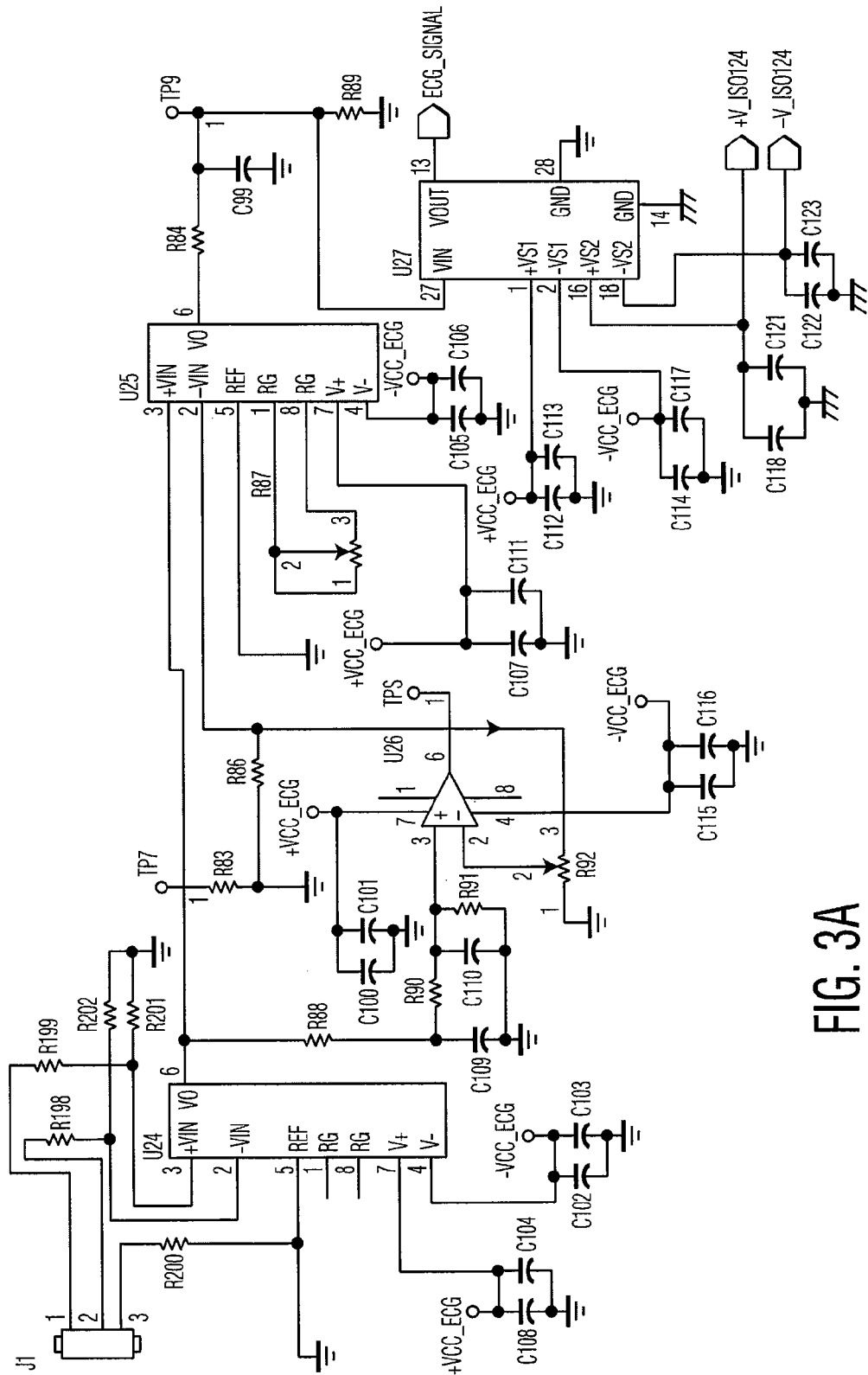
FIG. 3A is a circuit diagram illustrating an exemplary electrocardiogram (ECG) signal conditioner shown in FIG. 1A, according to an embodiment of the present invention.

FIG. 3A is a circuit diagram illustrating an exemplary ECG signal conditioner 105 shown in FIG. 1A, according to an embodiment of the present invention. Table 1 provides circuit components and component values, according to an exemplary embodiment of the present invention. The ECG signal conditioner 105 includes a differential amplifier that amplifies one or more differential voltages among or between the multiple ECG electrodes. The conditioned analog ECG signal is provided to the connection module 132 of data acquisition system 108.

TABLE 1

ECG Signal Conditioner Circuit Values

| | |
|---|---|
| R202 | 1200 Ω |
| R201 | 4500 Ω |
| R84 | 12 kΩ |
| R87 | 20 kΩ |
| R200 | 22 kΩ |
| R83, R86, R198, R199 | 33 kΩ |
| R92 | 50 kΩ |
| R89 | 82 kΩ |
| R88, R90, R91 | 560 kΩ |
| C99, C101, C103, C104, C106, C111, C113, C116, C117, C121, C123 | 100 nF |
| C100, C102, C105, C107, C108, C112, C114, C115, C118, C122 | 1 µF |
| C109, C110 | 4.7 µF |
| U24 (Gain of 5 Instrumentation Amplifier) | AD8225 |
| U25 (Low Power Instrumentation Amplifier) | INA128 |
| U26 (Operational Amplifier) | OP27 |
| U27 (Isolation Amplifier) | ISO124/SO |
| J1 (Connector) | 3-Pin |

Figure 3B:
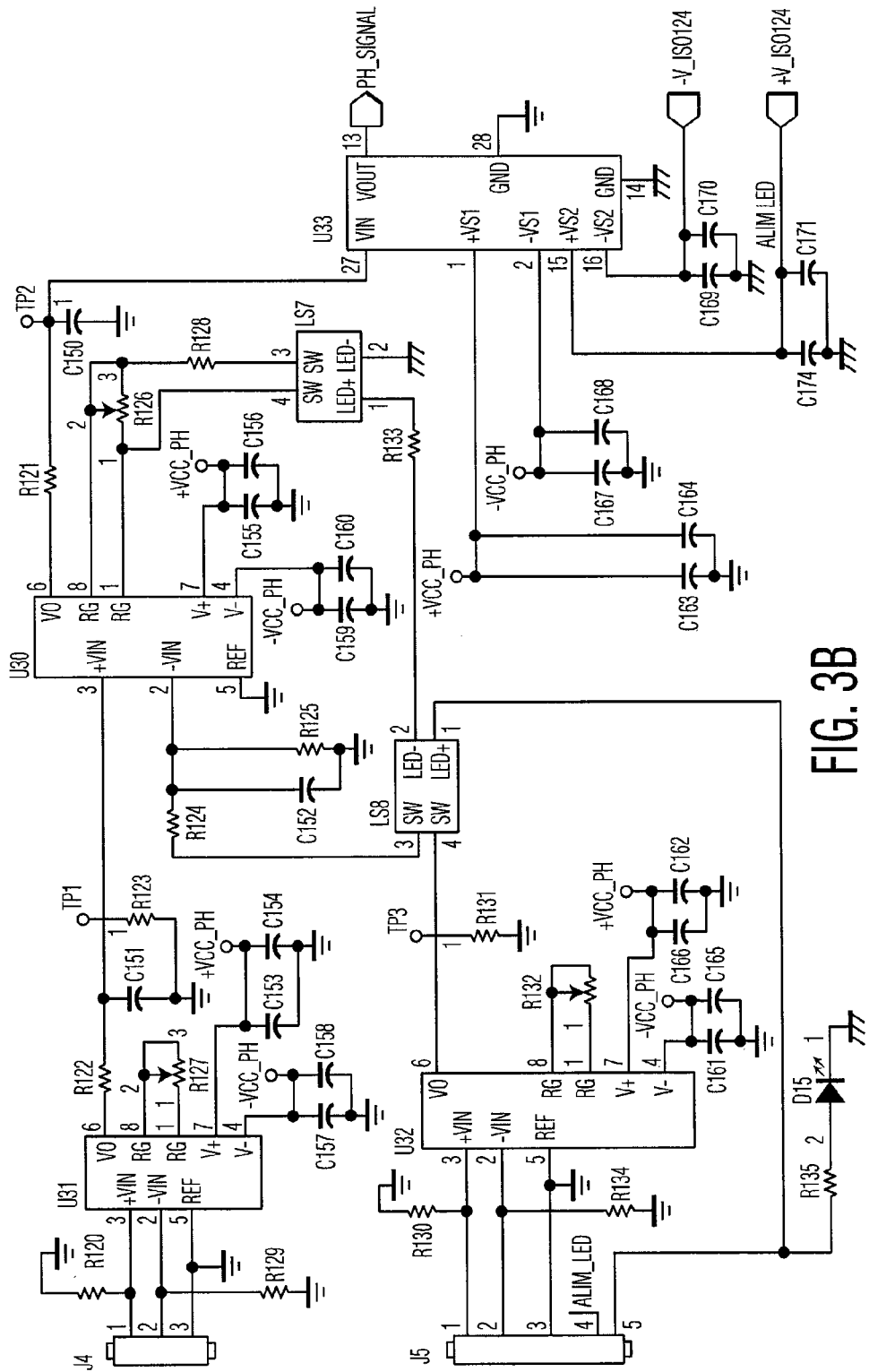
FIG. 3B is a circuit diagram illustrating an exemplary PCG signal conditioner shown in FIG. 1A, according to an embodiment of the present invention.

FIG. 3B is a circuit diagram illustrating an exemplary PCG signal conditioner 106 shown in FIG. 1A, according to an embodiment of the present invention. Table 2 provides circuit components and component values, according to an exemplary embodiment of the present invention. Although FIG. 1A illustrates a single PCG sensor 104, in an exemplary embodiment two PCG sensors 104 may be provided to PCG signal conditioning circuit 106, as shown in FIG. 3B. Each of the PCG sensors 104 is desirably the same model number having substantially identical frequency and sensitivity characteristics. Each of the PCG sensors is desirably configured as described above with respect to FIG. 2A such that each sensor 204 is placed in separate covers 206 (FIG. 2A) and separately attached to the chest wall. The first PCG sensor 104 is desirably placed on the chest wall at a location for maximum heart sound transmission. The second PCG sensor 104 is desirably placed close to the first PCG sensor 104 but in a position in which the heart sounds are substantially attenuated with respect to the first PCG sensor 104.

The PCG signal conditioner 106 may include a noise reduction circuit to determine a difference between the first and second PCG sensors 104 and, thus, reduce any background noise common to both PCG sensors 104. Common background noise may include, for example, blood flow or breathing noise.

In an exemplary embodiment, the PCG signal conditioner 106 includes a band-pass filter that passes frequencies within a range of about 15 Hz to 550 Hz, and, in particular, in a range of 20-550 Hz. In an exemplary embodiment, the PCG signal conditioner 106 uses a filter that approximates a rectangular window filter in order to suppress components outside of the typical frequency range of the PCG signal.

The PCG signal conditioner 106 of PCG sensor 104 may amplify the PCG signal and provide an impedance matching function to match an impedance of PCG sensor 104 to data acquisition system 108. The PCG signal conditioner may further include a gain control circuit that adjusts the gain of the PCG signal based on whether the DAQ/analysis controller 134 determines that the digitized PCG signal is saturated.

TABLE 2

PCG Signal Conditioner Circuit Values

| | |
|---|---|
| R128 | 820 Ω |
| R135 | 1200 Ω |
| R133 | 2.2 kΩ |

TABLE 2-continued

PCG Signal Conditioner Circuit Values

| | |
|---|---|
| R121, R122, R124 | 4.7 kΩ |
| R126, R127, R132 | 20 kΩ |
| R123, R125 | 33 kΩ |
| R120, R129, R130, R134 | 47 kΩ |
| R131 | 100 kΩ |
| C150, C151, C152 | 10 nF |
| C154, C156, C158, C160, C162, C164, C165, C168, C170, C171 | 100 nF |
| C153, C155, C157, C159, C161, C163, C166, C167, C169, C174 | 1 μF |
| U30, U31, U32 (Low Power Instrumentation Amplifier) | INA128 |
| D15 | LED |
| J4 (Connector) | 3-Pin |
| J5 (Connector) | 5-Pin |
| LS7, LS8 (PhotoMOS Relay) | AQY210 |
| U33 (Isolation Amplifier) | ISO124/SO |

A suitable ECG sensor 102, PCG sensor 104, signal conditioner 106, data acquisition system 108, PAP analyzer 110, storage means 126, storage means 131, display 128 and control interface 130 for use with the present invention will be understood by one of skill in the art from the description herein.

The exemplary apparatus 100 may provide a noninvasive method for estimating the PAP that is easy to use by physicians, nurses, technicians, paramedics, researchers or any one of skill in the art. A user may be easily trained to use the apparatus in a relatively short time period. For example, the apparatus 100 may not require significant set up time and may be configured to acquire data and estimate the PAP for frequent and/or continuous monitoring of a patient without discomfort for the patient. The exemplary apparatus 100 reliably and consistently yields real time values of PAP, for example, for the diagnosis, evaluation, and monitoring of pulmonary artery hypertension estimated, noninvasively, from the analysis of the S2 recorded with a PCG sensor. Health related personnel can be quickly trained to manage the exemplary apparatus 100 in different patient settings, including noisy environments.

The apparatus 100 may be used as a desktop or handheld instrument. The apparatus 100 may be implemented on different types and sizes of computers as well as computers having different processing power capabilities. Hardware upgrades and/or software upgrades, for example algorithm modifications, may be provided. The analyzed data may be reviewed off-line for research purposes and/or further evaluation of patient data.

The exemplary apparatus 100 may also provide signal acquisition and, thus, analysis that is not significantly affected by environmental noise and/or noise provided by other devices present, for example, a mechanical respirator or an aortic pump.

Figure 4:
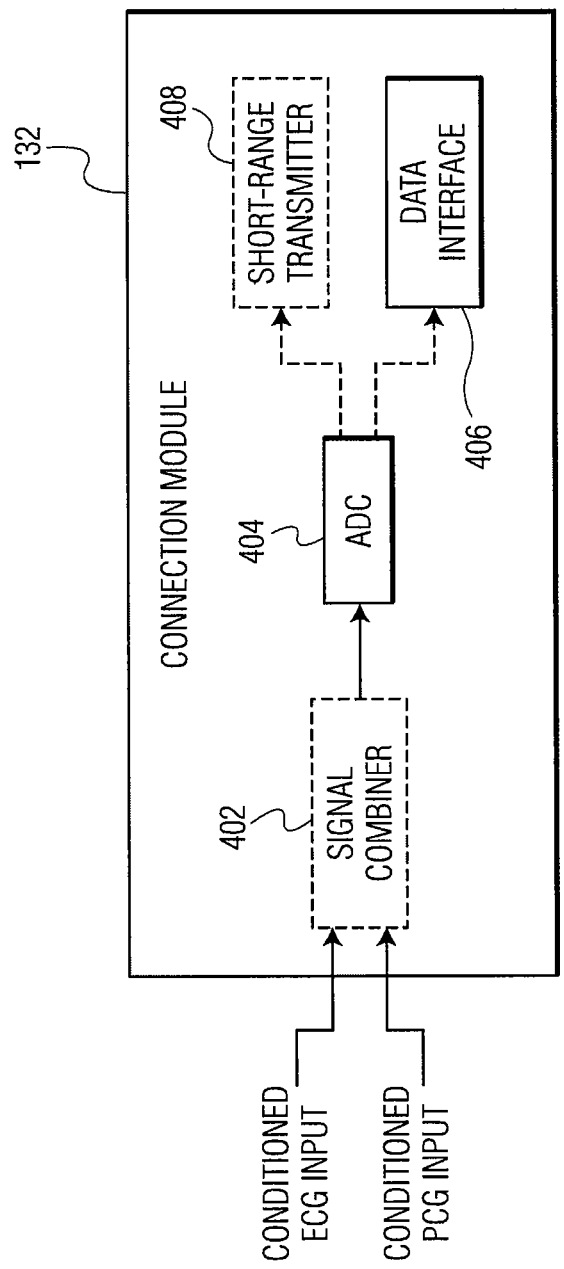
FIG. 4 is a functional block diagram illustrating an exemplary connection module shown in FIG. 1B, according to an embodiment of the present invention.
Figure 5:
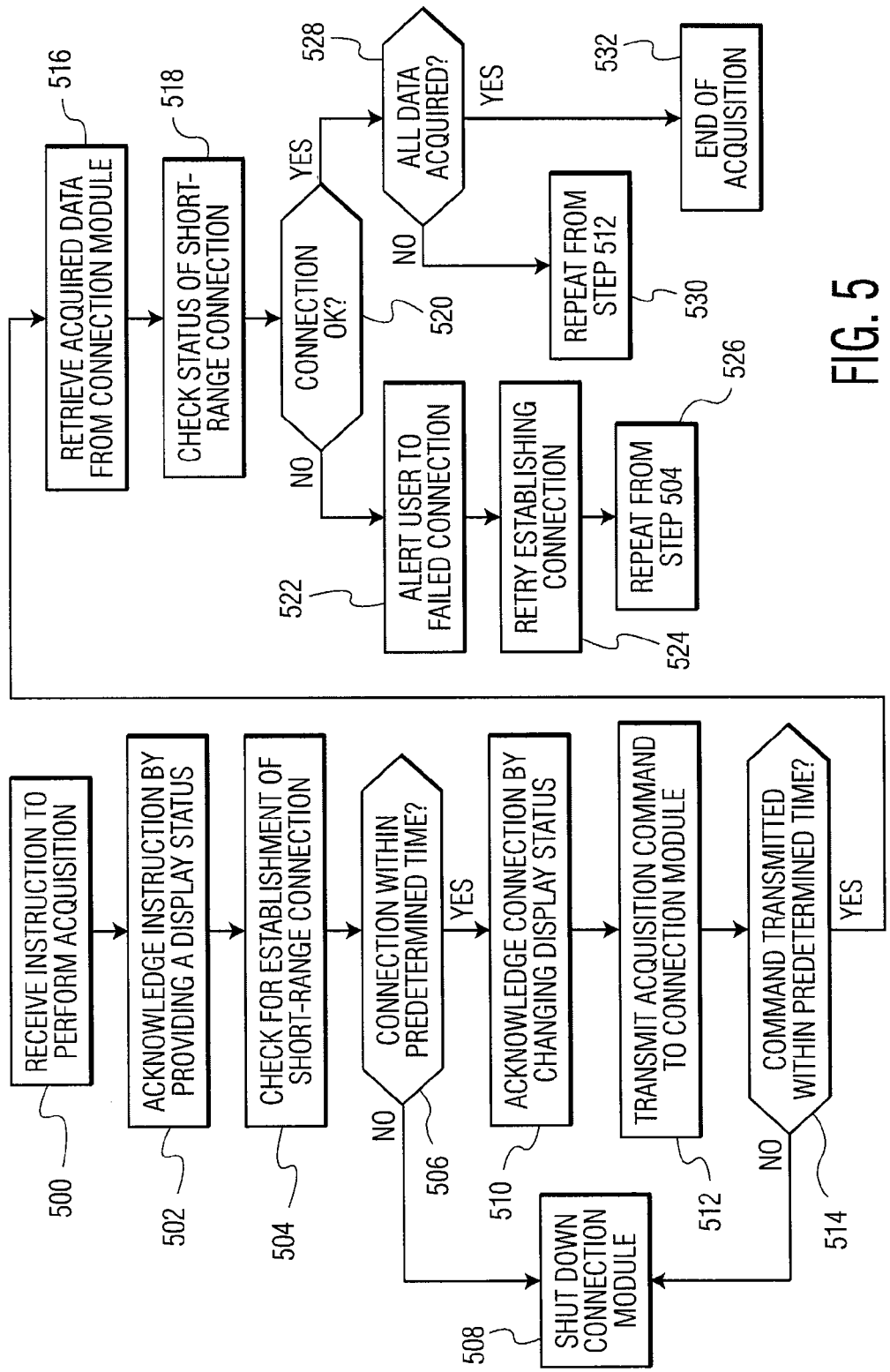
FIG. 5 is a flow chart illustrating an exemplary method for performing data acquisition using an exemplary connection module shown in FIG. 4, according to an embodiment of the present invention.

As described above, a system and methods are presented for determining a PAP estimate from one or more sets of ECG and corresponding PCG signals. Referring now to FIGS. 4 and 5, an exemplary connection module having an optional short-range connection and a method for acquiring data using the exemplary connection module are described below.

FIG. 4 is a functional block diagram illustrating an exemplary connection module 132 generally described with respect to FIG. 1B. In an exemplary embodiment, connection module 132 receives the conditioned ECG and PCG signals from respective ECG signal conditioner 105 and PCG signal conditioner 106 and converts the analog signals to digital signals with an ADC 404. The digitized signals may be transmitted to the DAQ/analysis controller 134 (FIG. 1B) using data interface 406. In an exemplary embodiment, data interface 406 includes a universal serial bus (USB) port capable of transmitting the digitized ECG and PCG signals separately using a stereo audio compression/decompression (codec) interface.

Optionally, the digitized signals may be transmitted to the DAQ/analysis controller 134 (FIG. 1B) using short-range transmitter 408, such as a Bluetooth transmitter such that the DAQ/analysis controller 134 (FIG. 1B) includes a short-range transceiver (not shown) capable of receiving the digitized PCG and ECG signals via a short-range connection. In one embodiment, the short-range transmitter 408 includes a Free2move F2M03Ac2-HP Bluetooth module and is capable of transmitting a single signal using a mono codec interface. Because the short-range transmitter may transmit a single signal, the conditioned ECG and PCG signals are combined using signal combiner 402 prior to digitization by ADC 404.

In one embodiment, signal combiner 402 applies a frequency modulation (FM) scheme to the conditioned ECG signal using an FM modulator (not shown). This FM modulated ECG signal is combined with the conditioned PCG signal, for example with a summation circuit, and provided to the ADC 404. Although an FM modulation scheme is illustrated, it is contemplated that any suitable method may be used to combine the conditioned ECG and PCG signals that maintains the desirable signal characteristics of each signal. It is contemplated that either the DAQ/analysis controller 134 (FIG. 1B) or the PAP analyzer 110 (FIG. 1A) may include an FM demodulator to demodulate the ECG signal from the single signal transmitted from the short-range transmitter 408. Although in an exemplary embodiment the FM modulation is provided at a frequency in a range between 1.6 kHz to 3.6 kHz, it is contemplated that any desirable FM frequency may be used.

In another embodiment, a stereo Bluetooth transmitter may be used as short-range transmitter 408. Because the short-range transmitter may transmit a stereo signal, the conditioned ECG and PCG signals may be provided to short-range transmitter 408 via ADC 404 without being combined by optional signal combiner 402.

FIG. 5 is a flow chart illustrating an exemplary method for performing data acquisition by the DAQ/analysis controller 134 (FIG. 1B), according to an embodiment of the present invention where the connection module 132 includes short-range transmitter 408 (FIG. 4) and DAQ/analysis controller 134 (FIG. 1B) includes a short-range transceiver (not shown). In step 500, an instruction is received to perform data acquisition. In an exemplary embodiment, control interface 130 (FIG. 1A) includes a push button for generating the data acquisition instruction and provides the instruction to DAQ/analysis controller 134 (FIG. 1B). In step 502, the DAQ/analysis controller 134 acknowledges receipt of the data acquisition instruction by providing a display status on display 128 (FIG. 1A). In an exemplary embodiment, this display status includes configuring an LED to emit a green color.

In step 504, the DAQ/analysis controller 134 checks for establishment of a short-range connection between the DAQ/analysis controller 134 and the connection module 132 within a predetermined time. Although in an exemplary embodiment this time period is two minutes, it is understood that this predetermined time may include any desirable communication establishment time. In an exemplary embodiment, the connection module 132 is configured to power off after two minutes in order to conserve battery power. In an exemplary embodiment, the predetermined time corresponds to the time period in which the connection module 132 is powered on.

In step 506 it is determined whether a connection is established within the predetermined time. If the connection is not established, step 506 proceeds to step 508 and the connection module 132 is shut down, i.e. powered off.

If the connection is established, step 506 proceeds to step 510. In step 510, the DAQ/analysis controller 134 acknowledges the connection by configuring the display 128 (FIG. 1A) to change its display status. In an exemplary embodiment, an LED displays a blinking blue color.

In step 512, the DAQ/analysis controller 134 transmits a start-acquisition command to connection module 132. In an exemplary embodiment, the connection module 132 includes a counter (not shown) that is used to count down to a time for powering off the connection module 132. The start-acquisition command from the DAQ/analysis controller 134 is used to reset the clock in order to maintain its powered on status. In step 514, it is determined whether the start-acquisition command is transmitted within the predetermined time, i.e. prior to shut down of the connection module 132. If the command is not transmitted within the predetermined time, step 514 proceeds to step 508 and the connection module is shut down, i.e. powered off.

If the command is transmitted within the predetermined time, step 514 proceeds to step 516. In step 516, the acquired data is retrieved by the DAQ/analysis controller 134 from the connection module 132.

In step 518, a status of the short-range connection is checked by the DAQ/analysis controller 134. Although step 518 is illustrated as occurring in sequential order with step 516, it is contemplated that step 518 may occur throughout the acquisition process. In step 520, it is determined whether a suitable short-range connection is provided.

If the connection fails, step 520 proceeds to step 522 and the DAQ/analysis controller 134 configures the display 128 to alert the user to the failed connection. In an exemplary embodiment, the display 128 includes an audio output such that both an LED is configured to emit a red color and a buzzer produces an audible output. It is contemplated that any suitable display and/or audio output may be provided to alert a user to a failed connection. In step 524, the DAQ/analysis controller 134 retries establishing a connection with the connection module 132. In step 526, the process is repeated from step 504.

If the connection is maintained, step 520 proceeds to step 528. In step 528, it is determined whether all of the data is acquired. For example, the control interface 130 (FIG. 1A) may select a number of ECG and PCG signal sets to be acquired for PAP analysis and provide this number of signal sets to the DAQ/analysis controller 134. If all of the data is not acquired, step 528 proceeds to step 530. In step 530, the process is repeated from step 512.

If all of the data is acquired, step 528 proceeds to step 532, and the acquisition is complete. In an exemplary embodiment, because the connection module 132 includes a counter (not shown) to automatically shut down, further action by the user via control interface 130 may not be needed to shut down the connection module 132.

Although not illustrated in FIG. 5, an exemplary embodiment of the present invention includes capability by the DAQ/analysis controller 134 to determine and alert a user (such as via display 128 (FIG. 1A) of a low battery condition, such as for connection module 132 (FIG. 1B). In an exemplary embodiment, if the battery charge becomes low, display 128 may configure an LED to display a blinking red color as well as configuring a buzzer (not shown) to produce an audible output. While the apparatus 100 (FIG. 1A) is in the low battery state, any in-progress measurements may be completed. After the measurement procedure is concluded, the DAQ/analysis controller 134 desirably permits only recharging of the battery.

During battery recharging, in an exemplary embodiment, the DAQ/analysis controller 134 configures an LED on the display 128 to emit a red color. The DAQ/analysis controller 134 desirably does not permit data acquisition during the recharging of the battery.

Although not illustrated in FIG. 5, an exemplary embodiment of the present invention further includes the capability by the DAQ/analysis controller 134 to determine whether the amplitude of the received PCG signal is saturated upon starting a data acquisition. If the PCG signal is saturated, the DAQ/analysis controller 134 may transmit a command to connection module 132, such as via a short-range transceiver, to adjust a gain within PCG signal conditioner 106. Although in an exemplary embodiment, saturation of the PCG signal received by the DAQ/analysis controller 134 is determined, it is contemplated that the DAQ/analysis controller 134 may determine whether the ECG signal is saturated, whether the PCG or ECG signal is too low, or any desirable combination of amplitude conditions.

Figure 6:
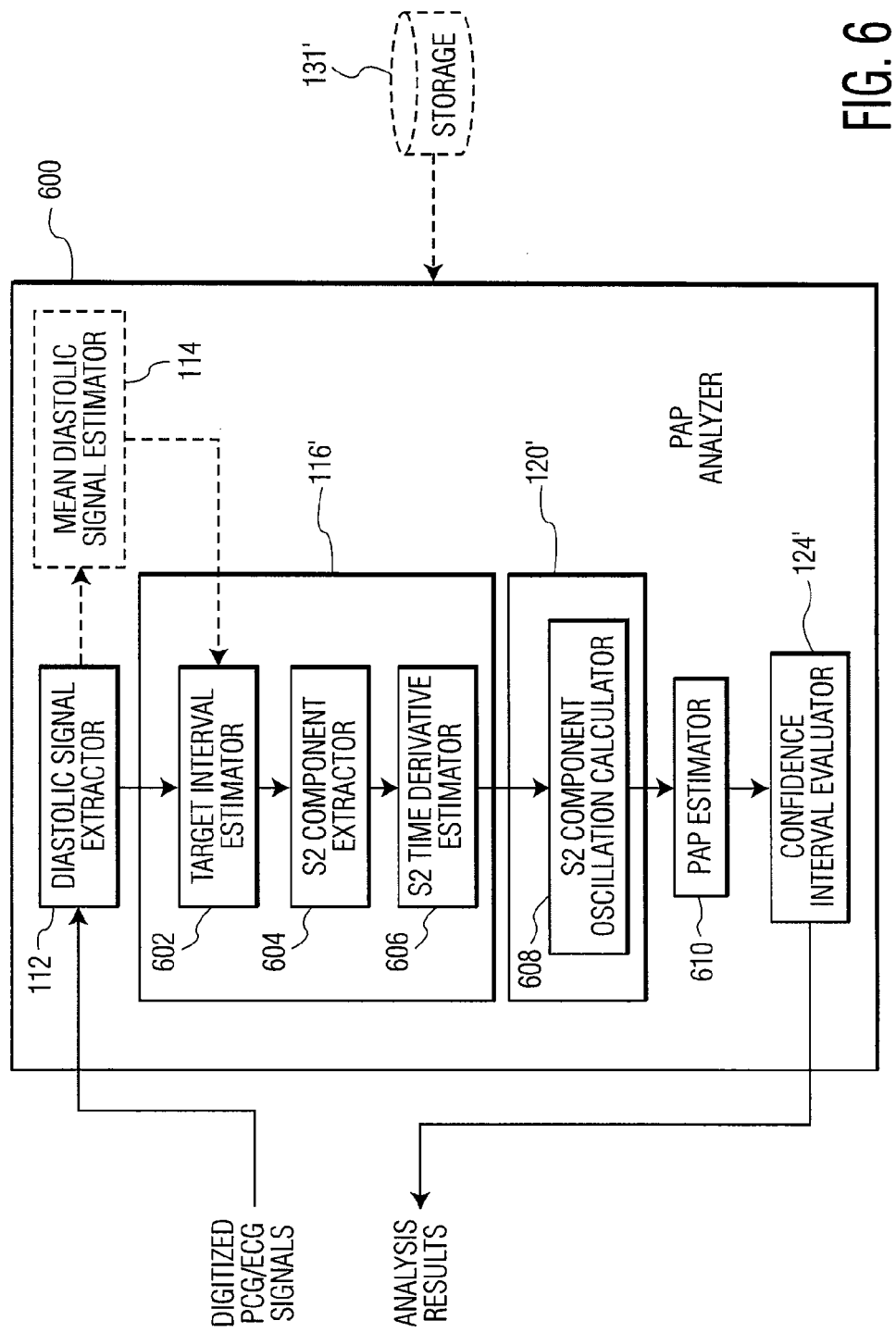
FIG. 6 is a functional block diagram illustrating an exemplary PAP analyzer for noninvasively estimating PAP according to a further embodiment of the present invention.

FIG. 6 is a functional block diagram illustrating an exemplary PAP analyzer 600 for noninvasively estimating PAP according to a further embodiment of the present invention. PAP analyzer 600 receives digitized PCG and digitized ECG signals from data acquisition system 108 (FIG. 1A). PAP analyzer 600 includes diastolic signal extractor 112 that is configured to extract a diastolic signal from the received digitized PCG signal using the received digitized ECG signal. As described below, the digitized ECG signal may be used to provide a timing window for extracting the diastolic signal from the digitized PCG signal. PAP analyzer 600 is the same as PAP analyzer 110 (FIG. 1A) except that PAP analyzer 600 calculates a number of oscillations in an S2 component using a target interval and generates a PAP estimate based on the number of oscillations in the S2 component.

The extracted diastolic signal is provided to time derivative estimator 116'. Time derivative estimator 116' is the same as time derivative estimator 116 (FIG. 1A), except that S2 time derivative estimator 116' extracts an S2 component and estimates the time derivative of the extracted S2 component and provides the time derivative of the S2 component to oscillation calculator 118'. Time derivative estimator 116' includes a target interval estimator 602, an S2 component extractor 604 and an S2 time derivative estimator 606.

Within time derivative estimator 116', target interval estimator 602 receives the extracted diastolic signal from diastolic signal extractor 112 and determines a target interval from the extracted diastolic signal such that the target interval includes the S2 component. The S2 component desirably includes the A subcomponent and the P subcomponent, discussed above. According to an exemplary embodiment, a number of oscillations in the S2 component within the diastolic signal may be calculated, using the target interval, and this number of oscillations may be used to generate a PAP estimate. The diastolic signal may include an isoelectric signal component, where the isoelectric signal component refers to a part of the diastolic signal without significant S2 component information. The isoelectric signal component may have a constant bias but may include a noise component. If a fixed time interval is used to extract the S2 component, the isoelectric signal component may contribute to the number of oscillations that are calculated. The isoelectric signal component, thus, may cause the PAP estimate to be incorrect. Accordingly, it is desirable to reduce the influence of the isoelectric signal component on the PAP estimate. In an exemplary embodiment, target interval estimator 602 may determine an onset time and an end time for the S2 component, described further below with respect to FIG. 8. The onset time and the end time may be used to form the target interval and the target interval may be provided to S2 component extractor 604.

S2 component extractor 604 receives the extracted diastolic signal, from diastolic signal extractor 112, and the target interval from target interval estimator 602 and extracts the S2 component from the extracted diastolic signal using the target interval. The extracted S2 component is provided to S2 time derivative estimator 606.

S2 time derivative estimator 606 receives the extracted S2 component from S2 component extractor 606 and estimates a time derivative of the extracted S2 component. S2 time derivative estimator 606 provides the time derivative of the S2 component to S2 component oscillation calculator 608 of oscillation calculator 120'.

Oscillation calculator 120' may be, for example, the same as oscillation calculator 120 (FIG. 1A) except that oscillation calculator 120' includes S2 component oscillation calculator 608. S2 component oscillation calculator 608 determines the number of oscillations using the time derivative of the S2 component that is extracted using the target interval. S2 component oscillation calculator 608 determines a number of oscillations in the extracted S2 component, received from S2 time derivative estimator 606, according to a time domain analysis of the S2 component. The number of oscillations determined by the S2 component oscillation calculator 608 is provided to PAP estimator 610.

PAP estimator 610 desirably generates a PAP estimate by applying a predetermined relationship between PAP and the number of oscillations received from S2 component oscillation calculator 608. PAP estimator 610 is the same as PAP estimator 122 (FIG. 1A) except that the predetermined relationship for PAP estimator 610, described below, is a function of the number of oscillations in the S2 component. It is contemplated that the predetermined relationship may be stored in a storage means 131' and retrieved by PAP estimator 610 during generation of the PAP estimate. The PAP estimate may also be provided to storage means 131', storage means 126 and/or display 128 (FIG. 1A).

In an exemplary embodiment, a predetermined number of PCG signals and corresponding ECG signals may be acquired from ECG sensor 102 and PCG sensor 104 using data acquisition system 108 (FIG. 1A) and processed by PAP analyzer 600 in order to reduce noise artifacts that may be encountered during a single PCG signal and corresponding ECG signal acquisition, as discussed above.

In an exemplary embodiment, PAP analyzer 600 may process the predetermined number of PCG signals and corresponding ECG signals to generate a plurality of PAP estimates. The plurality of PAP estimates may be stored in storage means 131'. PAP analyzer 600 may include a confidence interval evaluator 124' to evaluate a confidence interval measure from the plurality of PAP estimates generated using the predetermined number of acquired signals, as discussed above. Confidence interval evaluator 124' is the same as confidence interval evaluator 124 (FIG. 1A) except that confidence interval evaluator 124' evaluates a confidence interval measure from PAP estimates based on the S2 component extracted using the target interval. The confidence interval measure may be provided by confidence interval evaluator 124' to storage means 131', storage means 126 and/or display 128 (FIG. 1A).

In an alternative embodiment, PAP analyzer 600 may include mean diastolic signal estimator 114 that may be configured to determine a mean diastolic signal from a plurality of extracted diastolic signals received from diastolic signal extractor 112 corresponding to the predetermined number of acquired signals, as described above with respect to FIG. 1C. In PAP analyzer 600, the mean diastolic signal from mean diastolic signal estimator 114 may be provided to target interval estimator 602 and used by S2 component extractor 604. Processing through PAP analyzer 600 blocks 606-124' may continue, as described above, using the mean diastolic signal determined by mean diastolic signal estimator 114.

Storage means 131' may store at least one of the PCG signal(s), the ECG signal(s), the extracted diastolic signal(s), the target interval(s), the extracted S2 component(s), the PAP estimate(s) or the confidence interval measure. It is contemplated that S2 time derivative estimator 606 may retrieve the extracted S2 component from storage means 131' and that mean diastolic signal estimator 114 shown in FIG. 1C may be used with storage means 131'. Storage means 131' is the same as storage means 131 (FIG. 1A) except that storage means 131' may store the extracted S2 component, the target interval, the PAP estimate, and/or the confidence interval measure according to the S2 component extracted using the target interval.

A PAP analyzer 600 and storage means 131' for use with the present invention will be understood by one of skill in the art from the description herein.

Figure 7:
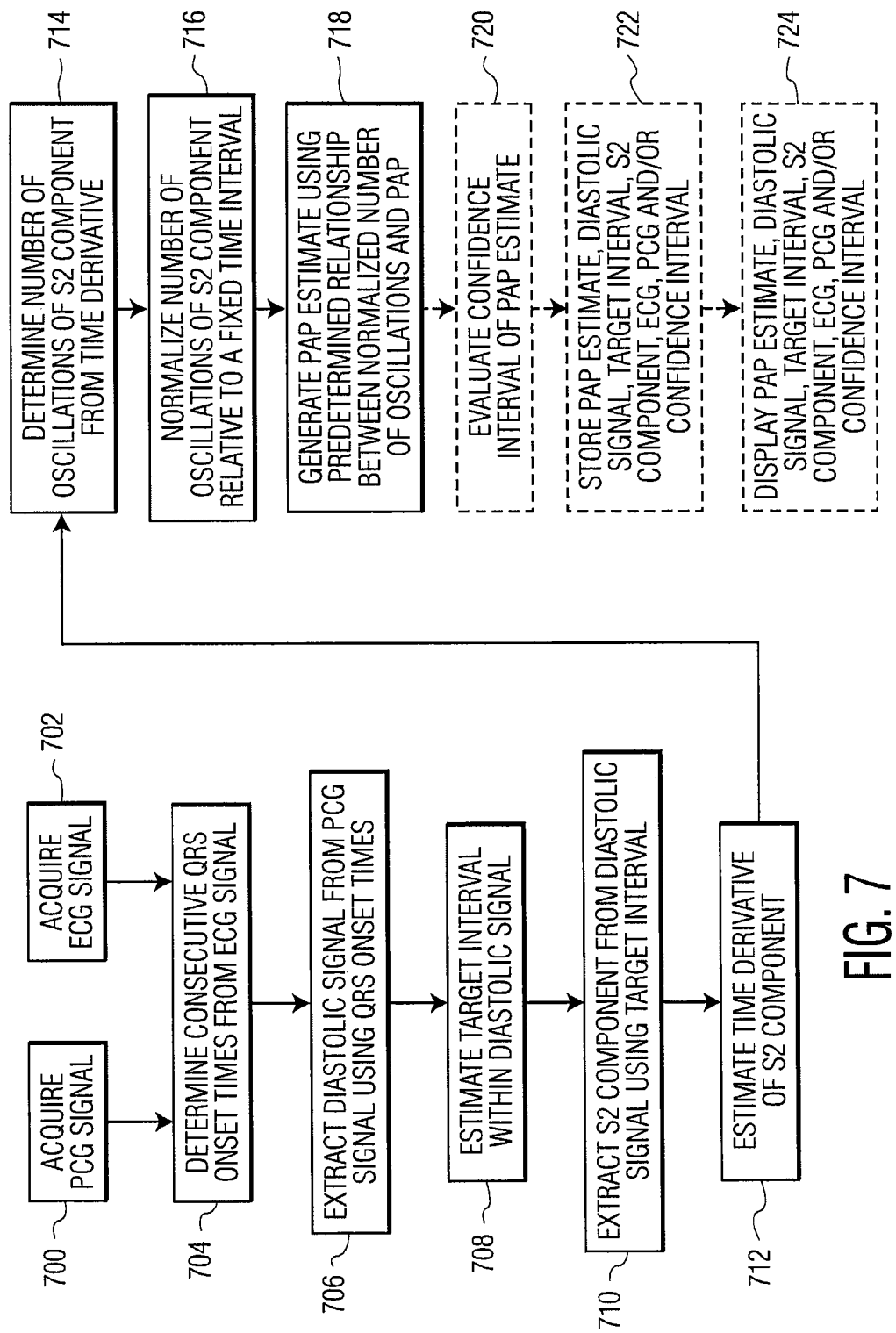
FIG. 7 is flow chart illustrating an exemplary method for noninvasively estimating PAP using the exemplary PAP analyzer shown in FIG. 6, according to a further embodiment of the present invention.
Figure 9A:
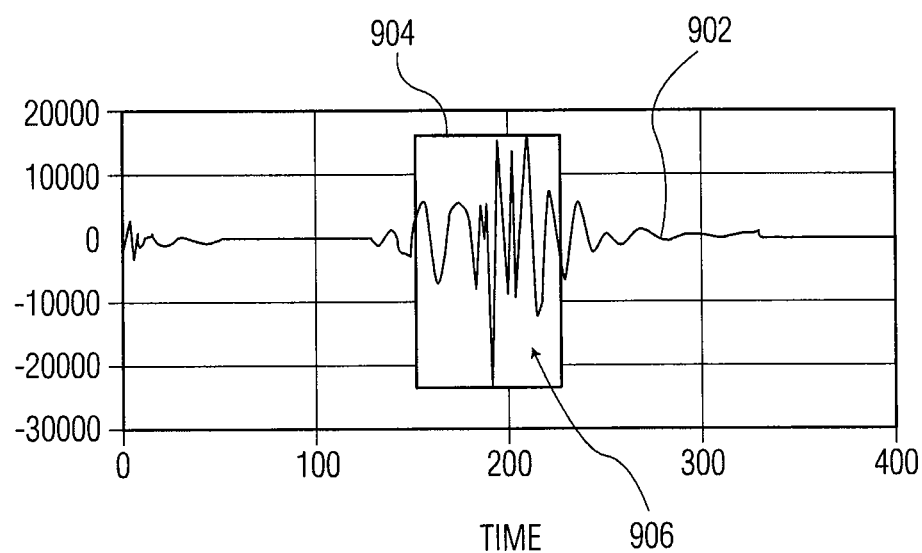
FIG. 9A is a graph of a signal amplitude versus time that is useful for illustrating extraction of an S2 component from a diastolic signal using a target interval according to the exemplary method shown in FIG. 7.
Figure 9B:
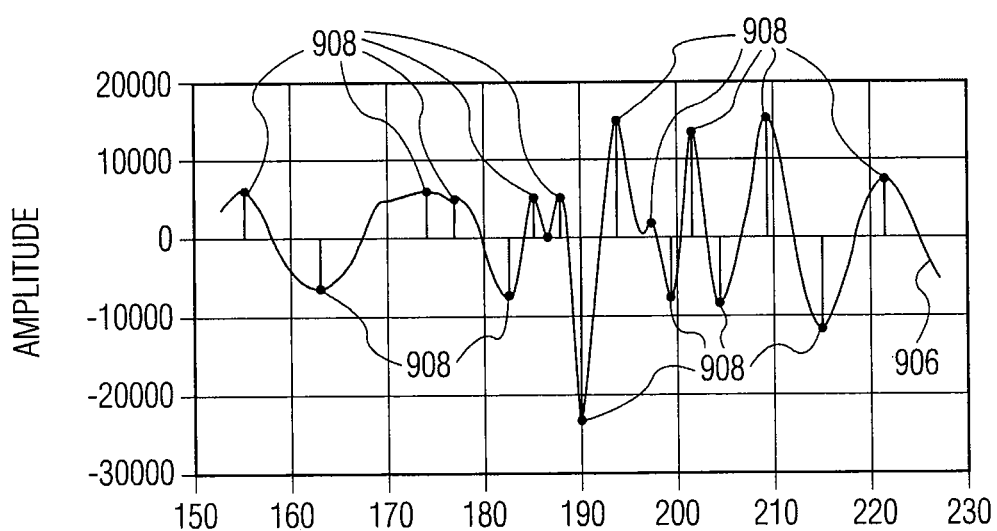
FIG. 9B is a graph of signal amplitude versus time that is useful for illustrating determination of a number of oscillations of the S2 component according to the exemplary method shown in FIG. 7.

FIG. 7 is flow chart illustrating an exemplary method for noninvasively estimating PAP using the exemplary PAP analyzer 600 shown in FIG. 6, according to a further embodiment of the present invention. The following figures illustrate examples of the exemplary method shown in FIG. 7: FIG. 9A is a graph of signal amplitude versus time that is useful for illustrating extraction of an S2 component from a diastolic signal using a target interval; and FIG. 9B is a graph of signal amplitude versus time that is useful for illustrating determination of a number of oscillations of the extracted S2 component.

Referring to FIG. 7, in step 700, a PCG signal is acquired and, in step 702, an ECG signal is acquired. The PCG signal and ECG signal are desirably synchronously acquired, for example, using data acquisition system 108 with ECG sensor 102 and PCG sensor 104 (FIG. 1A).

In step 704, two consecutive QRS complex onset times are determined using known in the art techniques from the ECG signal. In an exemplary embodiment, the first two consecutive QRS complex onset times are used to extract the diastolic signal. It is understood that any pair of QRS complex onset times may be used to extract the diastolic signal. The QRS complex onset times may be used to define an interval containing a diastolic signal within the PCG signal. For example, a first QRS complex onset time, $T_f$, and a second QRS complex onset time, $T_g$, may be determined from the ECG signal.

In step 706, a diastolic signal is extracted from the PCG signal using the determined QRS complex onset times $T_f$ and $T_g$. For example, a time interval, $T_e$, may be calculated from the two QRS complex onset times. An S2 onset time for the diastolic signal may be determined according to the calculated time interval, $T_e$. In an exemplary embodiment, a time interval, $T_q$, corresponding to a quarter of time interval $T_e$ may be used as the S2 onset time.

A predetermined portion of the PCG signal beginning with the S2 onset time is extracted as the diastolic signal. In an exemplary embodiment, the predetermined portion corresponds to 330 ms. The inventors have determined that a diastolic signal is included within a 330 ms portion of the PCG signal having an S2 onset time corresponding to $T_q$. It is contemplated that any suitable portion of the PCG signal that includes at least the S2 component of the diastolic signal may be used in order to extract a diastolic signal. The extracted diastolic signal may further be normalized. Steps 704 and 706 may be performed by diastolic signal extractor 112 (FIG. 6).

In step 708, a target interval is determined from the extracted signal such that the target interval includes the S2 component, for example, by target interval estimator 602 (FIG. 6). Target interval determination is described further below with respect to FIG. 8.

In step 710, the S2 component is extracted from the extracted diastolic signal using the target interval determined in step 708, for example by S2 component extractor 604 (FIG. 6). Referring to FIG. 9A, an extracted diastolic signal 902 and a target interval 904 are shown. An S2 component 906 may be extracted from diastolic signal 902 using target interval 904 and, for example, may be provided to S2 time derivative estimator 606 (FIG. 6).

Referring back to FIG. 7, in step 712, a time derivative of the extracted S2 component is estimated (referred to as a time derivative signal), for example using S2 time derivative estimator 606 (FIG. 6). In an exemplary embodiment, a first order time derivative signal is estimated in order to calculate a number of oscillation in the extracted S2 component based on a change in sign of the first order time derivative. In an exemplary embodiment, a first order time derivative signal is estimated according to eq. (1) as:

$$d(i)=[s(i+1)-s(i)] \cdot f_s \quad (1)$$

where d(i) represents the first order time derivative signal, i represents a sample index and $f_s$ represents the sampling rate. It is known to one of skill in the art that the first time derivative illustrates a trend in an angular coefficient of a line tangent to a signal at each time instant so that a change in sign of the first time derivative corresponds to the location where a signal reaches its maximum or minimum. It is contemplated that any of a number of well known numerical methods may be used to estimate the time derivative and that a higher order time derivative may be estimated in order to calculate a number of oscillations of the extracted S2 component.

In step 714, a number of oscillations of the S2 component is determined from the time derivative signal, for example using S2 component oscillation calculator 608 (FIG. 6). Referring to FIG. 9B, the extracted S2 component 906 is shown. The S2 component 906 includes a number of oscillations represented generally by points 908. The number of oscillations is related to various vibration modes, and is directly related to the highest frequency components of the S2 component. According to a further exemplary method of the present invention, a fundamental vibration mode and an overall contribution of higher-order vibration modes in the time domain are desirably used by counting the number of oscillations that occur within the extracted S2 component, where the target interval may be used to substantially suppress the contribution of the isoelectric signal component. By using the higher-order vibration modes in addition to the fundamental vibration mode, a right shift (i.e. a shift toward higher frequencies) of the spectral bandwidth as well as an enlargement of the spectral bandwidth (due to the contribution of the higher-order vibration modes) may be taken into account.

In step 716, the number of oscillations determined in the target interval are normalized relative to a fixed time interval. For example, the fixed time interval may be a predetermined time interval used in the target interval determination (step 708), described below with respect to FIG. 8. Because the determined target interval is variable, it may be difficult to compare the number of oscillations calculated for each individual to a predetermined relationship (based on a number of individuals) between the number of oscillations and PAP. Accordingly, the number of oscillations in the target interval may be converted to a number of oscillations in a fixed time interval. The number of oscillations, thus, may be normalized relative to the fixed time interval. For example, the target interval may be determined to have a 30 ms duration and 6 oscillations may be calculated in the 30 ms long target interval. A normalized number of oscillations in a 100 ms duration time interval may be approximated as 20 (i.e., 100 ms*6 oscillations/30 ms).

Referring back to FIG. 7, in step 718, a PAP estimate is generated using a predetermined relationship between the normalized number of oscillations and PAP, for example with PAP estimator 610 (FIG. 6). In general, the relationship can be presented as given by equation (2) as:

$$PAP \text{ Estimate} = a1 \cdot \left(a2^{\left(\frac{N}{a3}+a4\right)}\right) \text{mmHg} \quad (2)$$

where parameters a1, a2, a3 and a4 may be determined experimentally, for example, as described in copending U.S. application Ser. No. 11/496,754. In an exemplary embodiment, a1=22, a2=2, a3=6 and a4=−2.

In step 720, a confidence interval measure of the PAP estimate is evaluated, for example, using confidence interval evaluator 124' (FIG. 6). The confidence interval measure may be evaluated for a predetermined number of PCG and corresponding ECG signals. In this embodiment, for a predetermined number of acquired PCG and ECG signals, a standard uncertainty may be determined as described in copending U.S. application Ser. No. 11/496,754.

If a plurality of PAP estimates are generated, a frequency distribution of the PAP estimates may be determined. A fixed interval, for example, 10 mmHg, around a median value of the plurality of PAP estimates may be used to evaluate the confidence interval measure. For example, the median PAP estimate, upper and lower limits of the fixed interval and the confidence interval measure may be presented. If the confidence interval measure is below a predetermined threshold, for example 40% confidence, a warning may be provided that the confidence of the PAP estimate is low.

In alternate step 722, one or more of the PCG signal, the ECG signal, the extracted diastolic signal, the target interval, the extracted S2 component, the PAP estimate and the confidence interval measure may be stored, for example in storage means 131' (FIG. 6) and/or storage means 126 (FIG. 1A). In alternate step 724, one or more of the PCG signal, the ECG signal, the extracted diastolic signal, the target interval, the extracted S2 component, the PAP estimate and the confidence interval measure may be displayed, for example on display 128 (FIG. 1A).

Figure 8:
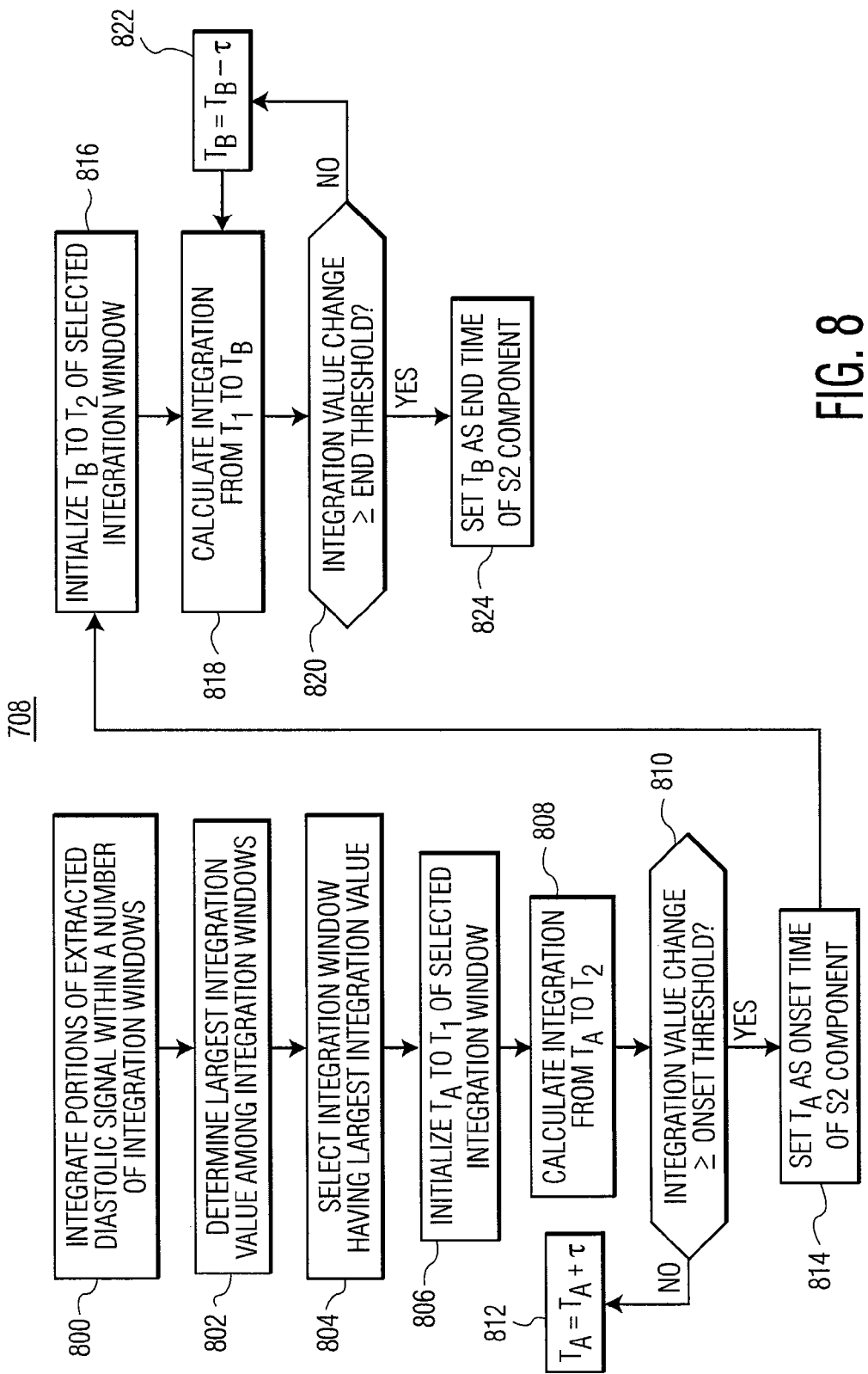
FIG. 8 is a flow chart an exemplary method for determining a target interval, according to an embodiment of the present invention.

FIG. 8 is a flow chart illustrating an exemplary method for determining a target interval, step 708 (FIG. 7), according to an embodiment of the present invention. In step 800, corresponding portions of the extracted diastolic signal are integrated within each of a number of integration windows to determine a number of respective integration values. An integration value for each portion of the diastolic signal may be determined by a summation of an absolute value of the corresponding portion of the diastolic signal in the integration window. The portion of the diastolic signal having the maximum integration value may represent a maximum energy of the diastolic signal and, thus, may include the S2 component. In an exemplary embodiment, the integration is performed with respect to an absolute value of the diastolic signal and using a moving window of about 0-20 ms, more particularly 0-13 ms. It is understood that any suitable moving window may be used to determine the integration value and that use of the absolute value of the S2 component is not meant to limit the scope of the invention. For example, a squared diastolic signal may be used for the integration. For digital integration, it is understood that the integration may be performed by any analog circuitry, any digital circuitry, any software or any combination thereof. It is contemplated that any number of well known numerical methods may be used to determine the respective integration values.

In an exemplary embodiment, each integration window has a predetermined time interval, $(T_1, T_2)$, with a duration to include at least an S2 component. The S2 component may have a duration between about 70-120 ms, depending upon the physical characteristics of the individual. Accordingly, in an exemplary embodiment, the predetermined time interval is between about 100-150 ms, and more particularly, about 100 ms. It is contemplated that any suitable duration may be used such that an integration window includes at least the S2 component. It is understood that the number of integration windows may depend upon the duration of each integration window and the duration of the extracted diastolic signal. Accordingly, any suitable number of integration windows may selected such that the duration of an integration window includes at least the S2 component.

In step 802, a largest integration value is determined from among the number of integrations windows. In step 804, the integration window having the largest integration value (also referred to as the maximum value of the selected integration window) is selected from among the number of integration windows. The integration window having the largest integration value may represent an integration window among the number of integration windows that includes the S2 component.

First, an onset time, $T_A$, of the target interval is determined. In step, 806, onset time $T_A$ is initialized to be equal to $T_1$ for the selected integration window. In step 808, an integration value is calculated for the selected integration window having integration limits of $(T_A, T_2)$.

In step 810, a change in the calculated integration value (step 808) (i.e. a decrease in the calculated integration value with respect to the maximum value) is compared to an onset threshold. If the integration value change is less than the onset threshold, step 810 proceeds to step 812 to increment the onset time, $T_A$ by a fixed time increment, τ, and steps 808-810 are repeated. Although in an exemplary embodiment, τ, is between about 1-5 ms, it is understood that τ may be any suitable value.

If the integration value change is greater than or equal to the onset threshold, step 810 proceeds to step 814. In step 814, the adjusted onset time $T_A$ is set as the onset time of the S2 component.

Next, an end time, $T_B$, of the target interval is separately determined for the selected integration window. In step 816, the end time $T_B$ is initialized to $T_2$ for the selected integration window. In step 818, an integration value is calculated for the selected integration window having integration limits of $(T_1, T_B)$.

In step 820, a change in the calculated integration value (step 818) (i.e. a decrease in the calculated integration value with respect to the maximum value) is compared to an end threshold. If the integration value change is less than the end threshold, step 820 proceeds to step 822 to decrement the end time, $T_B$ by the fixed time increment, τ, and steps 818-820 are repeated.

If the integration value change is greater than or equal to the end threshold, step 820 proceeds to step 824. In step 824, the adjusted end time $T_B$ is set as the end time of the S2 component. Accordingly, the target interval, $(T_A, T_B)$, may be used to extract the S2 component.

Although in an exemplary embodiment, the onset and end threshold are each about 5-20%, and more specifically about 10%, it is contemplated that any suitable onset threshold and end threshold may be selected to reduce the influence of the isoelectric signal component for PAP estimation. Although an exemplary embodiment sets the end threshold equal to the onset threshold, it is understood that the onset threshold may be different from the end threshold.

Figure 10:
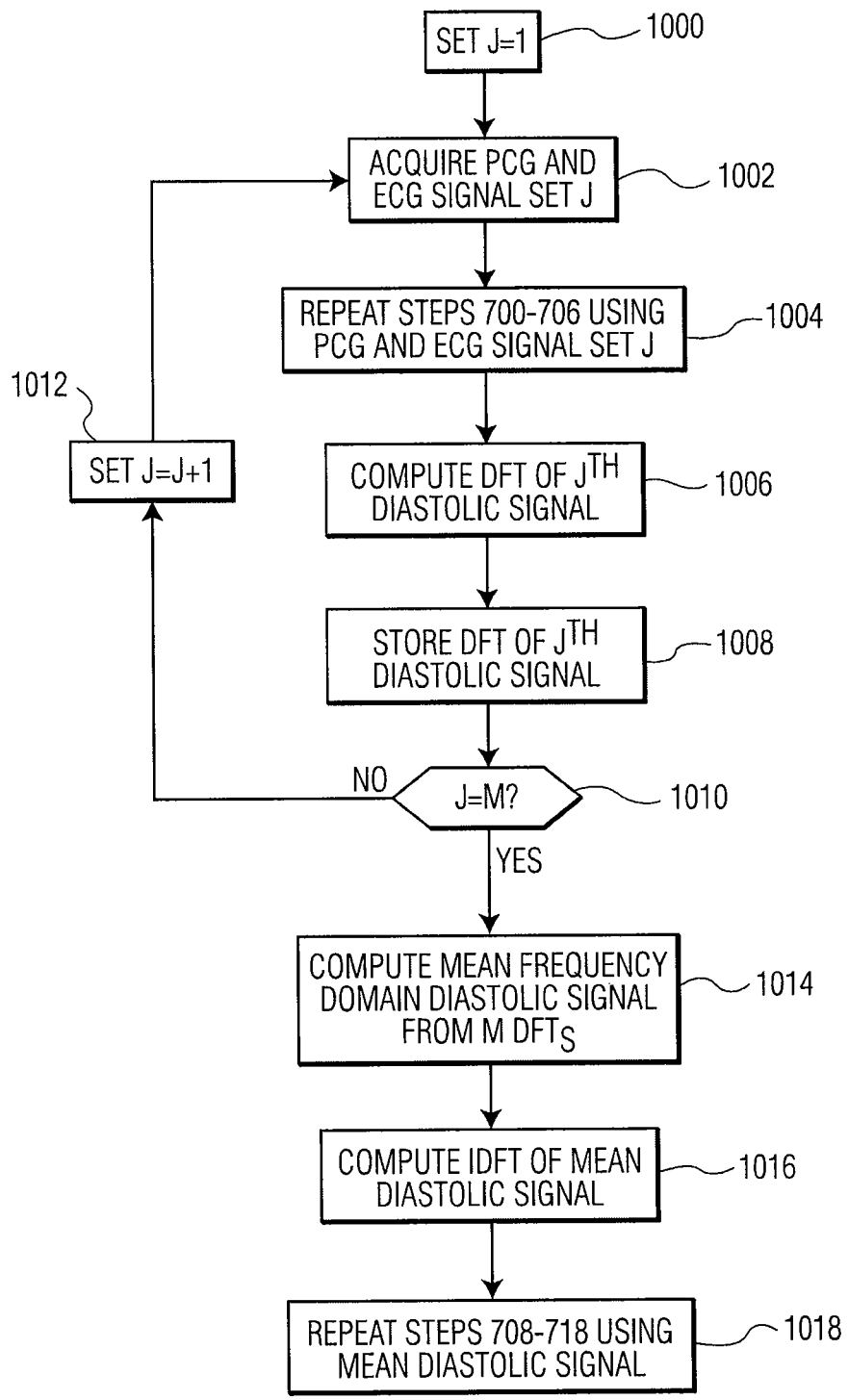
FIG. 10 is a flow chart illustrating an exemplary method for generating a PAP estimate from a plurality of acquired PCG and ECG signals using the exemplary PAP analyzer shown in FIG. 6, according to an embodiment of the present invention.
Figure 11:
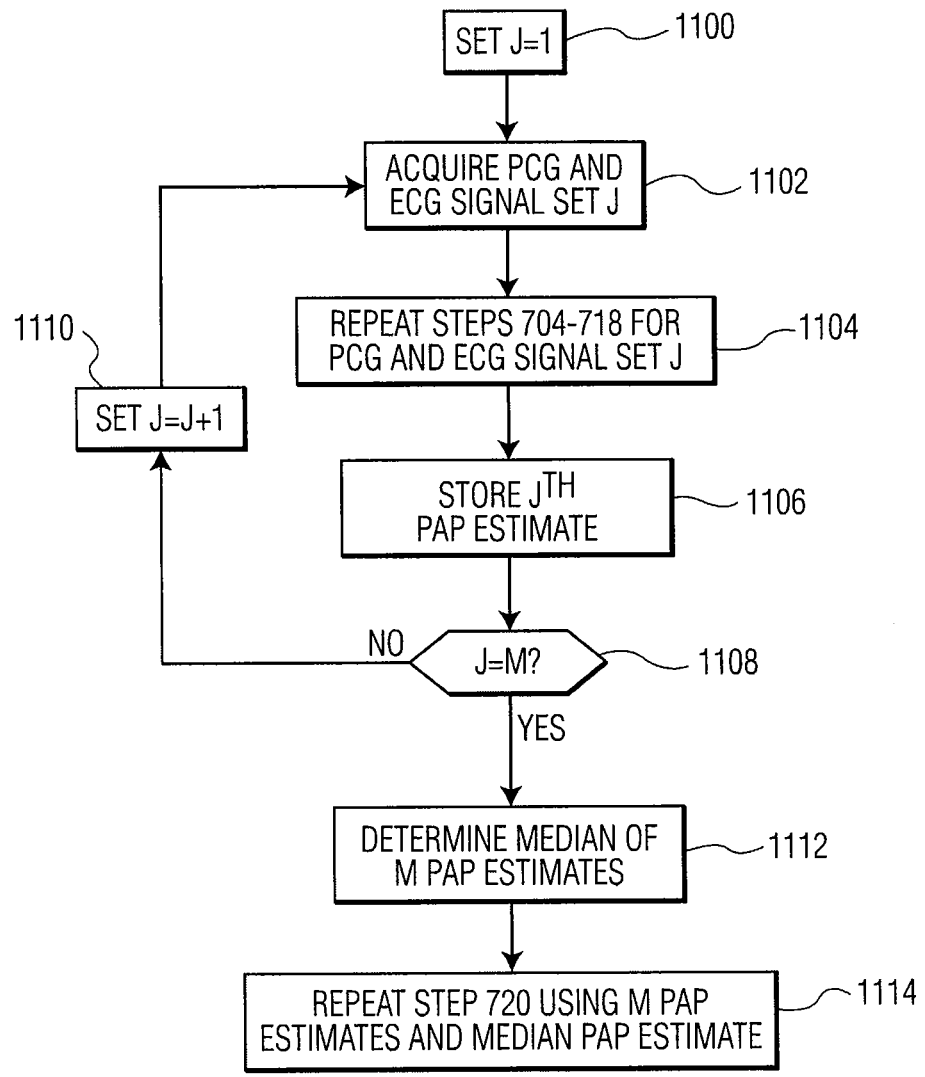
FIG. 11 is a flow chart illustrating an exemplary method for generating a PAP estimate from a plurality of acquired PCG and ECG signals using the exemplary PAP analyzer shown in FIG. 6, according to a further embodiment of the present invention.

As described above, a predetermined number of PCG signals and corresponding ECG signals may be acquired and a PAP estimate may be determined from the plurality of acquired sets of signals. Referring now to FIGS. 10 and 11 alternate exemplary embodiments are illustrated for generating a PAP estimate from the plurality of acquired sets of signals.

FIG. 10 is a flowchart illustrating an exemplary method for generating a PAP estimate using a predetermined number of acquired PCG and ECG signals using the exemplary PAP analyzer shown in FIG. 6, according to an embodiment of the present invention. In step 1000, a variable J is initialized. The variable J represents a $J^{th}$ signal set of the predetermined number, M, of PCG and corresponding ECG signals to be acquired. In step 1002, PCG and ECG signal set J are synchronously acquired, for example using data acquisition system 108 (FIG. 1A). In step 1004, steps 700-706 (FIG. 7) are repeated using PCG and ECG signal set J in order to extract the $J^{th}$ diastolic signal corresponding to signal set J.

In step 1006, a DFT signal of the $J^{th}$ extracted diastolic signal is computed, for example using DFT processor 136 (FIG. 1C). In step 1008, the DFT signal of the $J^{th}$ diastolic signal, (herein DFT(J)), is stored, for example, in storage means 131' (FIG. 6).

In step 1010, it is determined whether the predetermined number M of signal sets have been acquired and processed. If fewer than M signal sets have been acquired, step 1010 proceeds to step 1012 to update the signal set variable J and steps 1002-1010 are repeated.

If the predetermined number M of signal sets have been acquired and processed, step 1010 proceeds to step 1014. In step 1014, a mean frequency-domain diastolic signal is computed from the M DFT signals. For example, the stored DFT signals may be provided to mean calculator 140 (FIG. 1C). In step 1016, an IDFT signal of the frequency-domain S2 is computed, for example using IDFT processor 142 (FIG. 1C) to form the time-domain mean diastolic signal.

In step 1018, steps 708-718 (FIG. 7) are repeated using the time-domain mean diastolic signal in order to generate a PAP estimate. It is contemplated that any of steps 722-724 (FIG. 7) may be repeated to store or display desired values and signals.

FIG. 11 is a flow chart illustrating an exemplary method for generating a PAP estimate using a plurality of acquired PCG and ECG signals using the exemplary PAP analyzer shown in FIG. 6, according to a further embodiment of the present invention. In step 1100, a variable J is initialized. The variable J represents a $J^{th}$ signal set of the predetermined number, M, of PCG and corresponding ECG signals to be acquired. In step 1102, PCG and ECG signal set J are synchronously acquired, for example using data acquisition system 108 (FIG. 1A). In step 1104, steps 704-718 (FIG. 7) are repeated using PCG and ECG signal set J in order to generate a $J^{th}$ PAP estimate corresponding to signal set J. In step 1106, the $J^{th}$ PAP estimate is stored, for example using storage means 131' (FIG. 6).

In step 1108, it is determined whether the predetermined number M of signal sets have been acquired and processed. If fewer than M signal sets have been acquired, step 1108 proceeds to step 1110 to update the signal set variable J and steps 1102-1108 are repeated.

If the predetermined number M of signal sets have been acquired and processed, step 1108 proceeds to step 1112. In step 1112, a median PAP estimate is determined from the M stored PAP estimates. In step 1114, step 720 (FIG. 7) is repeated to determine a confidence interval measure using the median determined in step 1112 and the M PAP estimates, using a frequency distribution as described above. It is contemplated that any of steps 722-724 (FIG. 7) may be repeated to store or display desired values and signals.

Although the invention has been described in terms of apparatus and methods for noninvasively estimating a PAP, it is contemplated that one or more components may be implemented in software on microprocessors/general purpose computers (not shown). In this embodiment, one or more of the functions of the various components may be implemented in software that controls a general purpose computer. This software may be embodied in a computer readable carrier, for example, a magnetic or optical disk, a memory-card or an audio frequency, radio-frequency, or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for noninvasively estimating a blood pressure, the method comprising:
    a) extracting a diastolic signal from a phonocardiogram (PCG) signal;
    b) determining a target interval from the diastolic signal such that the target interval of the diastolic signal includes an S2 component;
    c) extracting the S2 component from the diastolic signal using the target interval, the extracted S2 component exhibiting a number of oscillations in the target interval;
    d) analyzing the extracted S2 component in the target interval to determine the number of oscillations in the extracted S2 component;
    e) applying a predetermined relationship between the determined number of oscillations and blood pressure to generate a blood pressure estimate; and
    f) displaying the blood pressure estimate.

2. The method according to claim 1, wherein step (b) includes the steps of:
    integrating a portion of the diastolic signal within an integration window to determine a first integration value, the integration window including at least the S2 component;
    adjusting an onset time of the integration window to determine a second integration value, the onset time being adjusted until a decrease in the second integration value relative to the first integration value is greater than or equal to an onset threshold; and
    separately adjusting an end time of the integration window to determine a third integration value, the end time being adjusted until a decrease in the third integration value relative to the first integration value is greater than or equal to an end threshold,
    wherein the adjusted onset time and the adjusted end time are used to define the target interval.

3. The method according to claim 2, wherein the integration window includes a number of integration windows and the method includes the steps of, prior to the step of integrating the portion of the diastolic signal:
    integrating corresponding portions of the diastolic signal within each of the number of integration windows to determine a number of respective integration values; and
    selecting the integration window having a largest integration value from among the number of integration windows.

4. The method according to claim 2, wherein the integration window is between about 100-150 ms.

5. The method according to claim 2, wherein each of the onset threshold and the end threshold are between about 5-20%.

6. The method according to claim 1, wherein the blood pressure includes a pulmonary artery pressure (PAP) and step (e) includes applying the predetermined relationship between the determined number of oscillations and PAP to generate a PAP estimate.

7. The method according to claim 1, wherein step (d) includes normalizing the number of oscillations in the target interval relative to a fixed time interval and step (e) includes applying the predetermined relationship between the normalized number of oscillations and the blood pressure to generate the blood pressure estimate.

8. The method according to claim 1, wherein step (d) includes determining the number of oscillations using a derivative with respect to time of the S2 component.

9. A non-transitory physical computer-readable carrier including computer instructions that cause a computer to perform the method according to claim 1.

10. The method according to claim 1, wherein the diastolic signal includes a plurality of diastolic signals and the blood pressure estimate is generated according to the plurality of S2 components of the respective plurality of diastolic signals.

11. The method according to claim 10, further including the step of determining a confidence interval measure associated with the blood pressure estimate.

12. The method according to claim 10, further including the steps of:
    repeating steps (b)-(e) over the plurality of diastolic signals to generate a corresponding plurality of blood pressure estimates; and
    determining a median of the plurality of blood pressure estimates to generate an average blood pressure estimate.

13. The method according to claim 10, wherein step (a) includes the step of:
    determining a mean diastolic signal from the plurality of diastolic signals,
    wherein steps (b)-(e) are performed using the mean diastolic signal.

14. The method according to claim 1, wherein step (a) includes the steps of:
    synchronously receiving the PCG signal and an electrocardiogram (ECG) signal; and
    extracting the diastolic signal from the received PCG signal using the received ECG signal.

15. The method according to claim 14, further including the step of determining a confidence interval measure associated with the blood pressure estimate.

16. The method according to claim 15, further including the step of storing at least one of the received PCG signal, the received ECG signal, the extracted diastolic signal, the target interval, the extracted S2 component, the confidence interval measure and the blood pressure estimate.

17. The method according to claim 15, wherein step (f) includes presenting, on a display device, the blood pressure estimate and at least one of the received PCG signal, the received ECG signal, the extracted diastolic signal, the target interval, the extracted S2 component and the confidence interval measure.

18. Apparatus for noninvasively estimating a blood pressure, the apparatus comprising:
   means for obtaining a diastolic signal from a phonocardiogram (PCG) signal;
   means for determining a target interval from the diastolic signal such that the target interval of the diastolic signal includes an S2 component;
   means for extracting the S2 component from the diastolic signal using the target interval, the extracted S2 component exhibiting a number of oscillations in the target interval;
   means for analyzing the extracted S2 component in the target interval to determine the number of oscillations in the extracted S2 component;
   means for applying a predetermined relationship between the determined number of oscillations and blood pressure to generate a blood pressure estimate; and
   means for displaying the blood pressure estimate.

19. Apparatus according to claim 18, wherein the blood pressure includes a pulmonary artery pressure (PAP) and the means for applying the predetermined relationship includes means for applying the predetermined relationship between the determined number of oscillations and the PAP to generate a PAP estimate.

20. Apparatus according to claim 18, the apparatus further comprising:
   means for receiving the PCG signal; and
   means for extracting the diastolic signal from the received PCG signal,
   wherein the means for determining the target interval includes means for determining the target interval from the extracted diastolic signal and the means for extracting the S2 component includes means for extracting the S2 component from the extracted diastolic signal.

21. Apparatus according to claim 18, wherein the means for analyzing normalizes the number of oscillations in the target interval relative to a fixed time interval and the means for applying the predetermined relationship applies the predetermined relationship between the normalized number of oscillations and the blood pressure to generate the blood pressure estimate.

22. A blood pressure analyzer for noninvasively estimating a blood pressure, the blood pressure analyzer comprising:
   a target interval estimator configured to determine a target interval from a diastolic signal such that the target interval includes an S2 component;
   a memory configured to store at least the S2 component that is extracted from the diastolic signal using the target interval, the extracted S2 component exhibiting a number of oscillations in the target interval;
   an S2 component oscillation calculator configured to determine the number of oscillations in the extracted S2 component using the target interval;
   a blood pressure estimator configured to apply a predetermined relationship between blood pressure and the number of oscillations determined by the S2 component oscillation calculator to generate a blood pressure estimate; and
   an output port configured to provide the blood pressure estimate and at least one of the diastolic signal, the target interval and the extracted S2 component.

23. The blood pressure analyzer according to claim 22, wherein the blood pressure includes a pulmonary artery pressure (PAP) and the blood pressure estimator is configured to generate a PAP estimate by applying the predetermined relationship between the PAP and the determined number of oscillations.

24. The blood pressure analyzer according to claim 22, the blood pressure analyzer further comprising:
   an input port for receiving a phonocardiogram (PCG) signal;
   a diastolic signal extractor coupled to the input port, the diastolic signal extractor configured to extract the diastolic signal from the PCG signal; and
   an S2 component extractor configured to extract the S2 component from the extracted diastolic signal using the target interval received from the target interval estimator,
   wherein the S2 component oscillation calculator is configured to determine the number of oscillations in the extracted S2 component from the extracted diastolic signal and to normalize the number of oscillations in the target interval relative to a fixed target interval, and
   the blood pressure estimator is configured to apply the predetermined relationship between blood pressure and the normalized number of oscillations received from the S2 component oscillation calculator.

25. The blood pressure analyzer according to claim 24, the blood pressure analyzer further comprising:
   an S2 time derivative estimator configured to receive the extracted S2 component from the S2 component extractor and to estimate the time derivative of the extracted S2 component,
   wherein the S2 component oscillation calculator is configured to determine the number of oscillations using the time derivative of the extracted S2 component received from the S2 time derivative estimator.

26. The blood pressure analyzer according to claim 24, the input port further configured to receive an electrocardiogram (ECG) signal corresponding to the PCG signal,
   wherein the diastolic signal extractor is configured to extract the diastolic signal using the corresponding ECG signal.

27. The blood pressure analyzer according to claim 26, wherein the memory further stores at least one of the received PCG signal, the received ECG signal, the extracted diastolic signal, the target interval and the blood pressure estimate.

28. The blood pressure analyzer according to claim 24, wherein:
   the PCG signal includes a plurality of PCG signals,
   the input port receives the plurality of PCG signals, and
   the blood pressure analyzer generates the blood pressure estimate according to the plurality of PCG signals received from the input port.

29. The blood pressure analyzer according to claim 28, further comprising a confidence interval evaluator configured to evaluate a confidence interval measure associated with the blood pressure estimate receive dorm the blood pressure estimator.

30. The blood pressure analyzer according to claim 28, wherein the diastolic signal extractor extracts a corresponding plurality of diastolic signals from the plurality of PCG signals and the blood pressure analyzer further comprises a mean diastolic signal estimator configured to estimate a mean diastolic signal from the plurality of extracted diastolic signals,
   wherein the target interval estimator uses the mean diastolic signal to determine the target interval and the S2 component extractor uses the mean diastolic signal to extract the S2 component.

* * * * *